US011237712B2

(12) United States Patent
Shinohara et al.

(10) Patent No.: US 11,237,712 B2
(45) Date of Patent: Feb. 1, 2022

(54) INFORMATION PROCESSING DEVICE, BIOMEDICAL-SIGNAL MEASURING SYSTEM, DISPLAY METHOD, AND RECORDING MEDIUM STORING PROGRAM CODE

(71) Applicant: Ricoh Company, Ltd., Tokyo (JP)

(72) Inventors: Michinari Shinohara, Kanagawa (JP); Hideaki Yamagata, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 24 days.

(21) Appl. No.: 16/133,821

(22) Filed: Sep. 18, 2018

(65) Prior Publication Data

US 2019/0129606 A1   May 2, 2019

(30) Foreign Application Priority Data

Oct. 31, 2017  (JP) .............................. JP2017-211019
Feb. 20, 2018  (JP) .............................. JP2018-027518

(51) Int. Cl.
*G06F 3/00* (2006.01)
*G06F 3/0484* (2013.01)
(Continued)

(52) U.S. Cl.
CPC ........ *G06F 3/04847* (2013.01); *A61B 5/0035* (2013.01); *A61B 5/0042* (2013.01);
(Continued)

(58) Field of Classification Search
CPC ................................. G06F 19/00; G06F 3/015
See application file for complete search history.

(56) References Cited

U.S. PATENT DOCUMENTS 4,744,029 A  *  5/1988  Raviv .................... A61B 5/048
                                                     600/544
5,515,301 A  *  5/1996  Corby, Jr ................ G06T 19/00
                                                     345/419
(Continued)

FOREIGN PATENT DOCUMENTS

JP     2000-287947 A      10/2000
JP     2008-232968        10/2008
(Continued)

OTHER PUBLICATIONS

Bajaj et al., "The Contour Spectrum," copyright 1997 IEEE, pp. 167-173. (Year: 1997).*

(Continued)

*Primary Examiner* — Amelia L Tapp
(74) *Attorney, Agent, or Firm* — Xsensus LLP

(57) ABSTRACT

Two types of information processing devices includes circuitry to display, on a display device, a position representation area indicating a position of each of a group of sensors that detects biomedical signals of a test subject, display on the display device a selection acceptance area accepting selection of a plurality of positions of a plurality of desired sensors, the plurality of positions being selected from the group of sensors using an operating unit, and display on the display device a waveform display area displaying a waveform output from the plurality of desired sensors corresponding to the plurality of selected positions. In the first type of information processing device, single-region data indicating a region including the plurality of selected positions is displayed in the position representation area. In the second type of information processing device, the plurality of selected positions are enlarged and displayed in the position representation area.

20 Claims, 26 Drawing Sheets

(51) Int. Cl.
*G06F 3/0482* (2013.01)
*G06F 3/0481* (2013.01)
*A61B 5/00* (2006.01)
*A61B 5/055* (2006.01)
*A61B 5/245* (2021.01)
*A61B 5/369* (2021.01)
*G06F 3/01* (2006.01)

(52) U.S. Cl.
CPC .............. *A61B 5/055* (2013.01); *A61B 5/245* (2021.01); *A61B 5/369* (2021.01); *A61B 5/743* (2013.01); *A61B 5/748* (2013.01); *A61B 5/7445* (2013.01); *G06F 3/015* (2013.01); *G06F 3/0481* (2013.01); *G06F 3/0482* (2013.01)

(56) References Cited

U.S. PATENT DOCUMENTS

| | | | | |
|---|---|---|---|---|
| 8,478,393 | B2* | 7/2013 | Ramanathan | A61B 5/04012 600/523 |
| 8,591,411 | B2* | 11/2013 | Banet | A61B 5/0002 600/300 |
| 9,500,485 | B2* | 11/2016 | Miichi | G01C 21/203 |
| 10,318,708 | B2* | 6/2019 | Balakrishnan | G16H 20/40 |
| 10,691,308 | B2* | 6/2020 | Bernini | G06F 3/0484 |
| 2004/0230118 | A1* | 11/2004 | Necola Shehada | A61B 5/0075 600/441 |
| 2012/0035685 | A1* | 2/2012 | Saha | A61N 1/37241 607/59 |
| 2017/0173262 | A1* | 6/2017 | Veltz | A61M 5/1723 |

FOREIGN PATENT DOCUMENTS

| | | |
|---|---|---|
| JP | 2009-118910 | 6/2009 |
| JP | 2011-153835 | 8/2011 |
| JP | 2018-089336 | 6/2018 |

OTHER PUBLICATIONS

Kirsch et al., "Experiments in Processing Pictorial Information with a Digital Computer" pp. 221-229, IRE-ACM-AIEE '57 (Eastern): Dec. 9-13, 1957. (Year: 1957).*

\* cited by examiner

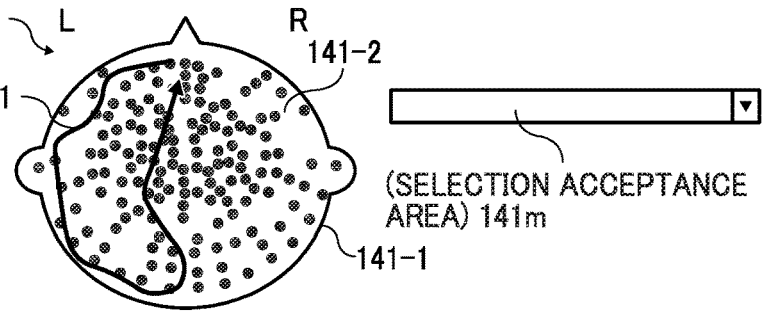
FIG. 7A
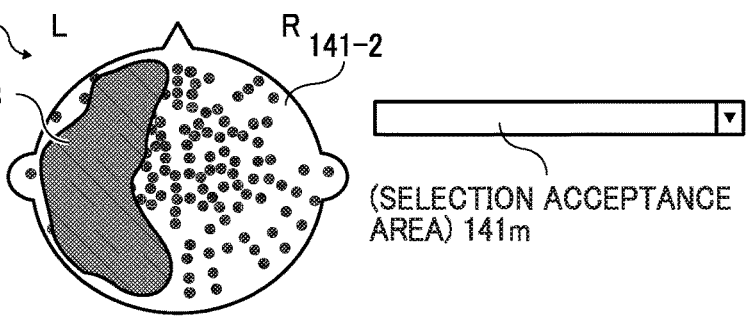
FIG. 7B
FIG. 7C
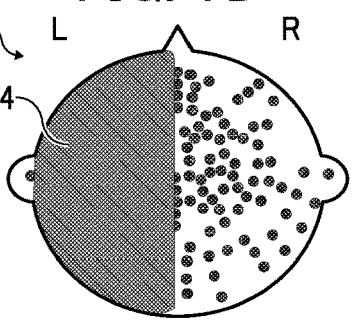
FIG. 7D (POSITION REPRESENTATION AREA/SELECTION ACCEPTANCE AREA) 141

(POSITION REPRESENTATION AREA/SELECTION ACCEPTANCE AREA) 141

(POSITION REPRESENTATION AREA/SELECTION ACCEPTANCE AREA) 141

(POSITION REPRESENTATION AREA/SELECTION ACCEPTANCE AREA) 141

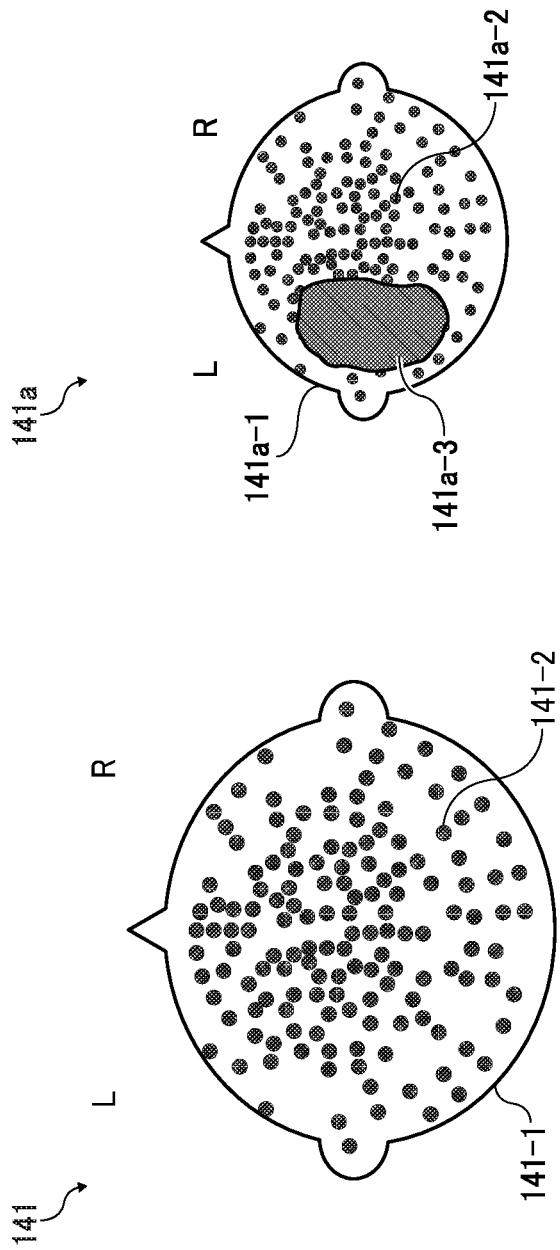

FIG. 12A
FIG. 12B
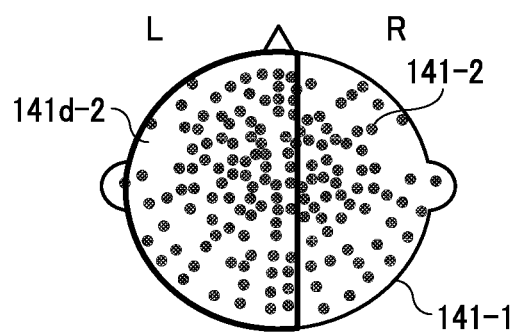
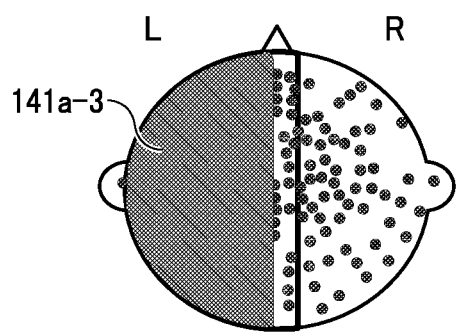
FIG. 12C
FIG. 12D
FIG. 12E
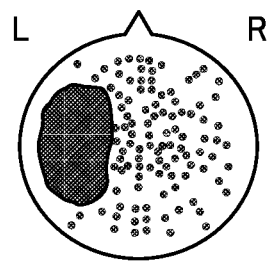
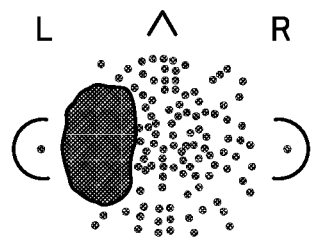
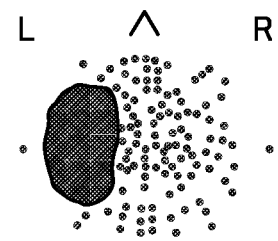

INFORMATION PROCESSING DEVICE, BIOMEDICAL-SIGNAL MEASURING SYSTEM, DISPLAY METHOD, AND RECORDING MEDIUM STORING PROGRAM CODE

CROSS-REFERENCE TO RELATED APPLICATIONS

This patent application is based on and claims priority pursuant to 35 U.S.C. § 119(a) to Japanese Patent Application Nos. 2017-211019 and 2018-027518, filed on Oct. 31, 2017, and Feb. 20, 2018, respectively, in the Japan Patent Office, the entire disclosures of which are hereby incorporated by reference herein.

BACKGROUND

Technical Field

Embodiments of the present disclosure relate to an information processing device, a biomedical-signal measuring system, a display method, and a recording medium storing program code for causing a computer to execute a display method.

Background Art

Currently, as non-invasive methods of recording the activity of the neurons of the brain noninvasively, there is a method of detecting the electrical activity of nerve cells of the brain with an electro-encephalograph and a method of detecting the magnetic field of the brain caused by the electrical activity with a magneto-encephalograph. Such methods are achieved as a measurement device provided with a group of sensors detects the biomedical signals of a test subject such as a human body. The detection results are processed by an information processing device such as a computer and then displayed on a display.

As a method of displaying the detection results, magneto-encephalograph systems are known in the art that display a channel selection screen through which desired sensors are selected and the waveforms that correspond to the selected sensors are displayed in a waveform display area. As the selected or specified sensors are colored, a technician can visually identify the sensors on the screen.

SUMMARY

Embodiments of the present disclosure described herein provide two types of information processing devices, a biomedical-signal measuring system, two types of display methods, and two types of recording media each storing program code for causing a computer to execute one of the two types of display methods. The two types of information processing devices and the two types of display methods include displaying, on a display device, a position representation area indicating a position of each of a group of sensors that detects biomedical signals of a test subject, displaying on the display device a selection acceptance area accepting selection of a plurality of positions of a plurality of desired sensors, the plurality of positions being selected from the group of sensors using an operating unit, and displaying on the display device a waveform display area displaying a waveform output from the plurality of desired sensors corresponding to the plurality of selected positions. In the first type of information processing device and the first type of display method, single-region data indicating a region including the plurality of selected positions is displayed in the position representation area. In the second type of information processing device and the second type of display method, the plurality of selected positions are enlarged and displayed in the position representation area. The biomedical-signal measuring system includes the information processing device and a measurement device provided with a group of sensors that detect biomedical signals of a test subject.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

FIG. 7A, FIG. 7B, FIG. 7C, and FIG. 7D are diagrams each illustrating a magneto-encephalogram distribution map according to an embodiment of the present disclosure.

FIG. 11A and FIG. 11B are schematic diagrams of a magneto-encephalogram distribution map and its downsized image, according to an embodiment of the present disclosure.

FIG. 12A to FIG. 12E are diagrams each illustrating a downsized image according to a modification of an embodiment of the present disclosure.

Figure 1:
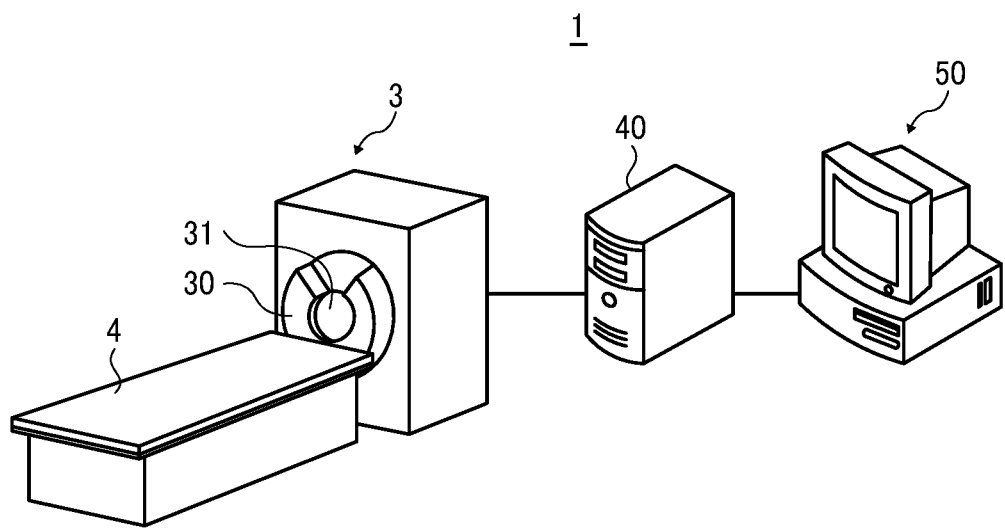
FIG. 1 is schematic diagram illustrating a biomedical-signal measuring system according to an embodiment of the present disclosure.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific-integrated-circuits (ASICs), field programmable gate arrays (FPGAs), computers or the like. These general elements may be collectively referred to as "processors".

Unless specifically stated otherwise, or is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

With reference to the drawings, an information processing device, a biomedical-signal measuring system, a display method, and a recording medium storing a program according to an embodiment of the present disclosure will be described below in detail.

FIG. 1 is schematic diagram illustrating a biomedical-signal measuring system 1 according to an embodiment of the present disclosure. The biomedical-signal measuring system 1 measures various kinds of biomedical signals of a test subject (person to be measured) such as magneto-encephalography (MEG) signals and electro-encephalography (EEG) signals, and displays the results of measurement. The biomedical signals to be measured are not limited to the magneto-encephalography (MEG) signals and electro-encephalography (EEG) signals as above, but may be, for example, any electrical signal that is caused by cardiac activity (i.e., any electrical signal that can be expressed in an electrocardiogram (ECG)). As illustrated in FIG. 1, the biomedical-signal measuring system 1 includes a measurement device 3 that measures at least one biomedical signal of a test subject, a server 40 that stores at least one biomedical signal measured by the measurement device 3, and an information processing device 50 that analyzes at least one biomedical signal stored on the server 40. In the present embodiment, the server 40 and the information processing device 50 are described as separate units. However, no limitation is indicated thereby. For example, at least some of the functions of the server 40 may be implemented by the information processing device 50.

In the present embodiment as illustrated in FIG. 1, A test subject lies on a measurement table 4 on his or her back with electrodes (or sensors) attached to his or her head to measure the electrical brain waves, and puts his or her head into a hollow 31 of a Dewar 30 of the measurement device 3. The Dewar 30 is a container of liquid helium that can be used at very low temperatures, and a number of magnetic sensors for measuring the brain magnetism are disposed on the inner surface of the hollow 31 of the Dewar 30. Note that such magnetic sensors for measuring the brain magnetism may be referred to simply as sensors. The measurement device 3 collects the electrical signals and the magnetic signals through the electrodes and the magnetic sensors, respectively, and outputs data including the collected electrical signals and magnetic signals to the server 40. Note that such collected electrical signals and magnetic signals may be referred to simply as "measurement data" in the following description of the present embodiment. The measurement data recorded on the server 40 is read and displayed by the information processing device 50, and is analyzed by the information processing device 50. As known in the art, the Dewar 30 combined with a magnetic sensor and the measurement table 4 is disposed inside a magnetically shielded room.

The information processing device 50 synchronizes and displays the waveform of the magnetic signals obtained through the multiple magnetic sensors and the waveform of the electrical signals obtained through the multiple electrodes on the same time axis. Among these signals, the magnetic signals indicate minute changes in magnetic field caused by the electrical activity of the brain. The magnetic field of the brain is detected by a high-sensitivity superconducting quantum interference device (SQUID). The electrical signals indicate the inter-electrode voltage value obtained for the electrical activity of nerve cells (i.e., the flow of ionic charge at the dendrites of neurons during synaptic transmission). These electrical signals and magnetic signals are examples of biomedical signals.

Figure 2:
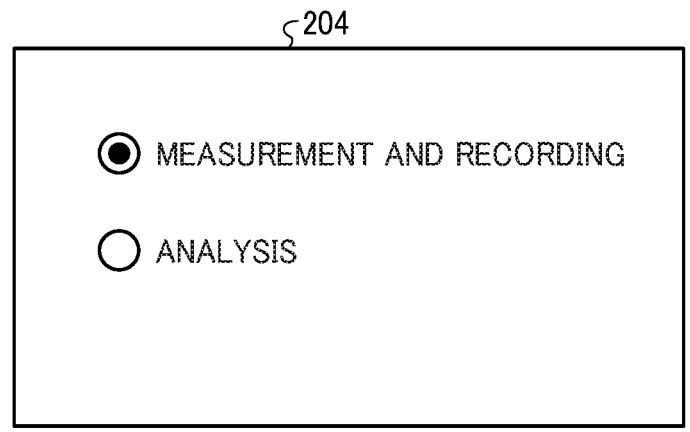
FIG. 2 is a diagram illustrating a starting screen displayed on an information processing device, according to an embodiment of the present disclosure.

FIG. 2 is a diagram illustrating a starting screen 204 displayed on the information processing device 50, according to the present embodiment.

On the starting screen 204, selection boxes "measurement and recording" and "analysis" are displayed. When the brain wave or brain magnetism is to be measured, in many cases, the person who measures and records the data and the subject who analyzes the data are different. For example, when the "measurement and recording" box is selected by a measurement engineer (technician), the data measured by the measurement device 3 is sequentially stored on the server 40, and is read and displayed by the information processing device 50. On the other hand, when the "analysis" box is selected by a physician after the measurement and recording is done, the recorded measurement data is read and analyzed.

Figure 3:
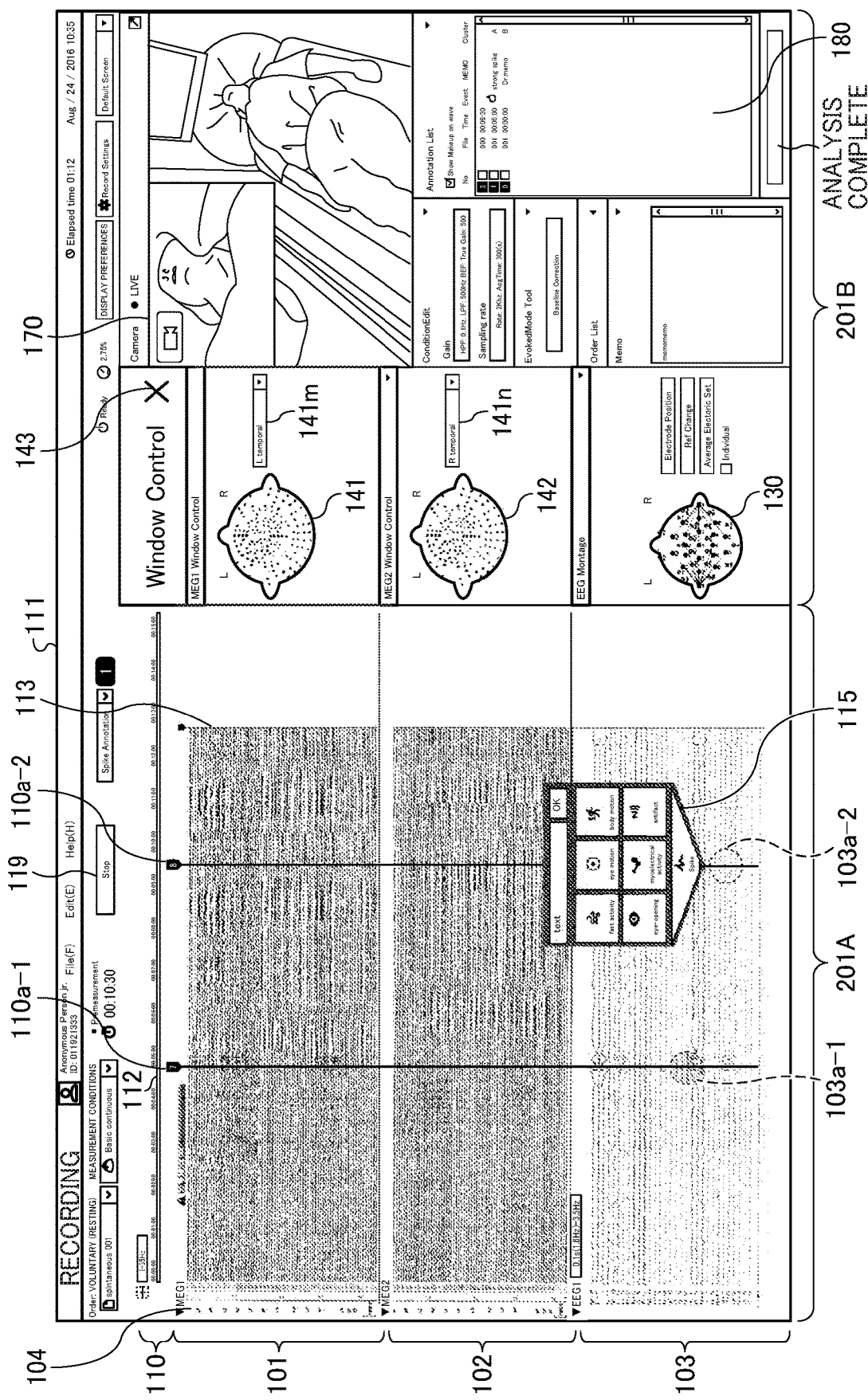
FIG. 3 is a diagram illustrating a measurement and recording screen according to an embodiment of the present disclosure.

FIG. 3 is a diagram illustrating a measurement and recording screen according to an embodiment of the present disclosure.

The measurement and recording screen includes an area 201A on which measured signal waveform is displayed, and an area 201B on which monitoring data other than the signal waveform is displayed. The area 201A on which signal waveform is displayed is arranged on the left side of the screen when viewed from the technician, and the area 201B on which monitoring data other than the signal waveform is displayed is arranged on the right side of the screen when viewed from the technician. Accordingly, there is an economy of motion between the movement of the mouse from the area 201A on the left side of the screen to the area 201B on the right side of the screen and the movement of the line of sight of a technician that follows the motion of a waveform (detected in real time and dynamically displayed from the left side of the screen to the right side of the screen), and the efficiency improves.

In the area 201B of the display screen, a monitoring window 170 is displayed to monitor the state of a subject during measurement. By displaying the live image of the subject while he/she is being measured, the reliability of the check and judgment of a signal waveform can be improved.

The area 201A includes a time-indicating area 110 in which the time data of signal detection is displayed in the horizontal direction (i e, the first direction) of the screen, and waveform display areas 101 to 103 in which a plurality of signal waveforms based on the signal detection are displayed in parallel in the vertical direction (i.e., the second direction) of the screen.

The time data that is displayed in the time-indicating area 110 is a time line including the time indication given along a time axis 112. However, no limitation is indicated thereby, and such a time line may only be a band-like or belt-like axis where no time (time in number) is displayed, or may only be the time (time in number) where no axis is given. Alternatively, a time line may be displayed by displaying a time axis under the waveform display area 103 in addition to time-indicating area 110 on the topside of the screen.

In the area 201A, a plurality of signal waveforms obtained by a plurality of similar kinds of sensors or various kinds of signal waveforms obtained by a group of a plurality of different kinds of sensors are displayed in a synchronous manner along the same time axis. For example, the waveforms of a plurality of magneto-encephalography (MEG) signals obtained from the right side of the head of a subject and the waveforms of a plurality of magneto-encephalography (MEG) signals obtained from the left side of the head of a subject are displayed parallel to each other in the waveform display area 101 and the waveform display area 102, respectively. In the waveform display area 103, the waveforms of a plurality of electro-encephalography (EEG) signals are displayed in parallel. These waveforms of a plurality of electro-encephalography (EEG) signals correspond to the voltage signals measured between pairs of electrodes. Each of these waveforms of a plurality of signals is displayed along a channel axis 104 in association with the identification number or channel number of the sensor through which the signal is obtained.

Once measurement is started and the measurement information from each sensor is collected, as time passes a signal waveform is displayed from left to right in each of the waveform display areas 101 to 103 in the area 201A. A line 113 indicates the measurement time (present time), and moves from the left side to the right side of the screen. Once the signal waveform display reaches the right end of the area 201A (i.e., until the right end of the time axis 112), the signal waveform gradually disappears from the left end of the screen to the right. Then, new signal waveforms are displayed at disappearing positions in sequence from the left side to the right side, and the line 113 also moves from the left end of the screen to the right. Together with the above changes on the display, the lapse of time is also displayed in the horizontal time-indicating area 110 along the time axis 112 as measurement progresses. Measurement and recording continues until the stop key 119 is touched or clicked.

In the present embodiment, when the technician (i.e., the person who records the data) notices, for example, irregularities in waveform and a singular point of amplitude on the signal waveform during the data recording, he/she can mark a problematic point or area on the signal waveform. The point or area of such a problematic point or area to be marked can be specified by moving a mouse cursor and clicking with a mouse. The specified point or area is highlighted on the signal waveforms of the waveform display areas 101 to 103, and the specified result is displayed along the time axis 112 of time-indicating area 110 in a relevant point in time or time range. The marking information including the display along the time axis 112 is stored together with the signal waveform data. The specified point corresponds to a particular time, and the specified area corresponds to a certain area including the particular time.

In the example illustrated in FIG. 3, an area including at least one channel is specified at a time t1 in the waveform display area 103, and the span of time including the time t1 is highlighted at the mark 103a-1. In association with the display of the mark 103a-1, an annotation 110a-1 that indicates the result of specification is displayed at the corresponding point in time in the time-indicating area 110. At a time t2, another point in waveform or an area around that point is marked in the waveform display area 103, and a mark 103a-2 is highlighted at that point (the time t2) or in the area around that point (the time t2) (where at least one of a time range or a plurality of waveforms is indicated). At the same time, an annotation 110a-2 is displayed at the corresponding point in time (time range) in the time-indicating area 110. Note that the term "annotation" indicates that related information is attached to certain data as an annotation. An annotation according to the present embodiment is displayed at least based on the specified time data in association with the position at which the waveform is displayed based on the time data. When a plurality of channels is displayed, the annotation according to the present embodiment may be displayed in association with the corresponding channel information.

Once the technician specifies another point in waveform or an area around that point in waveform at the time t2, the mark 103a-2 is highlighted at the specified point, and an annotation number "2" is displayed at the corresponding point in time in the time-indicating area 110. Further, a pop-up window 115 for selecting the attribute is displayed at the highlighted point. The pop-up window 115 includes selection keys (buttons) for selecting the various kinds of attributes, and an input box through which a comment or additional information is input. On the selection keys, the causes of irregularities in waveform, such as fast activity, eye motion, body motion, or spike, are indicated as the attribute of waveform. As the technician can check the state of the subject through the monitoring window 170 of the area 201B in the screen, he/she can appropriately select the attribute indicating the causes of irregularities in waveform. For example, when a spike occurs in a waveform, the technician can determine whether such a spike is a symptom of epilepsy or caused by some other body movement (such as a sneeze) of the subject.

Some of or all of the annotation 110a-1, for example, at least one of an attribute icon and a text annotation, may be displayed near the mark 103a-1 on the signal waveforms in the waveform display area 103. When such an annotation is added directly over the signal waveforms, the ability to check the shape of the waveforms may be impaired. For this reason, when an annotation is displayed over the signal waveforms in the waveform display areas 101 to 103, it is desired that display or non-display of such an annotation be selectable.

In the monitoring window 170 of the area 201B, the live image of a state in which a subject lies on the measurement table 4 and the head of the subject is inside the measurement device 3 is displayed. In the area 201B, the magneto-encephalogram distribution maps 141 and 142 and the brain-wave distribution map 130, which correspond to the signal waveforms of the waveform display areas 101, 102, and 103, respectively, and the annotation list 180 are displayed.

The magneto-encephalogram distribution maps 141 and 142 are magneto-encephalogram distribution maps. The brain-wave distribution map 130 is a brain-wave distribution map that indicates the arrangement of electrodes (or sensors) to measure the brain waves. Before measurement and recording is performed, the magnetic sensors whose outputs are to be displayed in the waveform display areas 101 and 102 can be selected on the magneto-encephalogram distribution maps 141 and 142.

The magnetic sensors may be selected not just between the right and left groups of sensors, but may be selected from any part of the brain, such as the parietal region, frontal lobe, or temporal lobe. When sensors at the parietal region in the magneto-encephalogram distribution map 141 are selected in "MEG1 Window Control," the sensors other than sensors at the parietal region in the magneto-encephalogram distribution map 142 are selected in "MEG2 Window Control." As a result, the identification numbers or channel numbers of the sensors displayed along the channel axis 104 become the numbers of sensors at the parietal region in the waveform display area 101, and become the numbers of the sensors other than sensors at the parietal region at a parietal region in the waveform display area 102.

The annotation list 180 is a list of annotations marked on the signal waveforms in the area 201A. Every time the point or area on the signal waveforms is specified in the waveform display areas 101 to 103 and an annotation is given, the associated information is sequentially added to the annotation list 180.

When the stop key 119 is selected (touched or clicked) and the measurement is terminated, the highlighted portion specified in the waveform display areas 101 to 103 is stored in association with the signal waveform. The annotation information displayed at the corresponding point in time in the time-indicating area 110 is also stored in association with the annotation number and the time. By storing the above display information, even if the technician and the analyst are different, the analyst can easily recognize and analyze a problematic portion.

Figure 4:
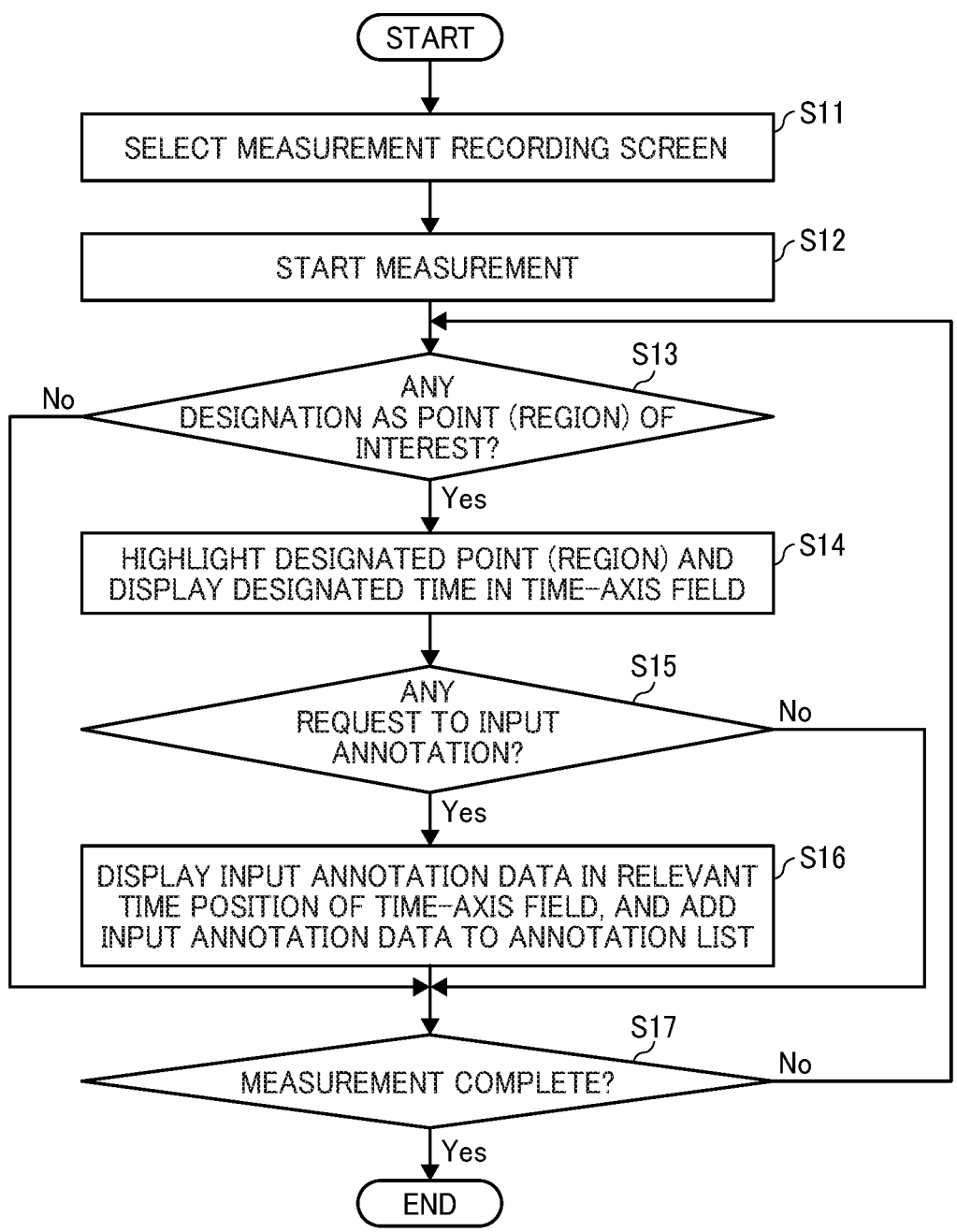
FIG. 4 is a flowchart of the operations performed by an information processing device during the measurement and recording, according to an embodiment of the present disclosure.

FIG. 4 is a flowchart of display information processing performed by the information processing device 50 in a stage of measurement and recording, according to the present embodiment.

When "measurement and recording" is selected on the starting screen 204 as illustrated in FIG. 2, an acceptance unit 52 of the information processing device 50 accepts the selection (step S11). Accordingly, the measurement is started, and the display controller 251 controls a display in a synchronous manner along a time axis where the waveforms of a plurality of signals are equivalent to each other (step S12). In the present embodiment, the term "a plurality of signal waveforms" includes both the signal waveform detected by a plurality of sensors of the same kind and the multiple signal waveforms detected by a plurality of various kinds of sensors. In the present embodiment, the waveforms of a plurality of biomedical signals consist of the waveform of the magnetic signals obtained through a plurality of magnetic sensors from the right side of the head of a subject, the waveform of the magnetic signals obtained through a plurality of magnetic sensors from the left side of the head of the subject, and the waveform of the electrical signals obtained through electrodes for measuring the electrical brain waves of the subject. However, no limitation is intended thereby.

A determining unit 55 of the information processing device 50 determines whether any point or area is designated a point of interest (or region of interest) in the displayed signal waveform (step S13). When some such designation is made (YES in S13), the display controller 251 controls the display to highlight the designated point (region) in the display areas of signal waveform (i.e., the waveform display areas 101 to 103), and display the results of selection in a relevant point in time of the time-axis field (i.e., the time-indicating area 110) (step S14). The results of selection include data indicating that the selection has been made or the identification information of the selection. The determining unit 55 determines whether or not there is a request to input an annotation at the same time the results of selection are displayed in the time-axis field or before or after the results of selection are displayed in the time-axis field (step S15). When there is a request to input an annotation (YES in the step S15), the display controller 251 displays the input annotation data in a relevant point in time of the time-axis field, and adds the input annotation data to the annotation list 180 so as to be displayed therein (step S16). Then, the determining unit 55 determines whether or not a measurement termination command has been input (step S17). On the other hand, when no point or area is designated a point of interest or a range of interest (NO in the S13) and when there is no request to input an annotation (NO in the step S15), the process proceeds to a step S17, and the determining unit 55 determines that measurement is completed. Until measurement is completed (YES in the S17), the processes in the steps S13 to S16 are repeated.

Figure 5:
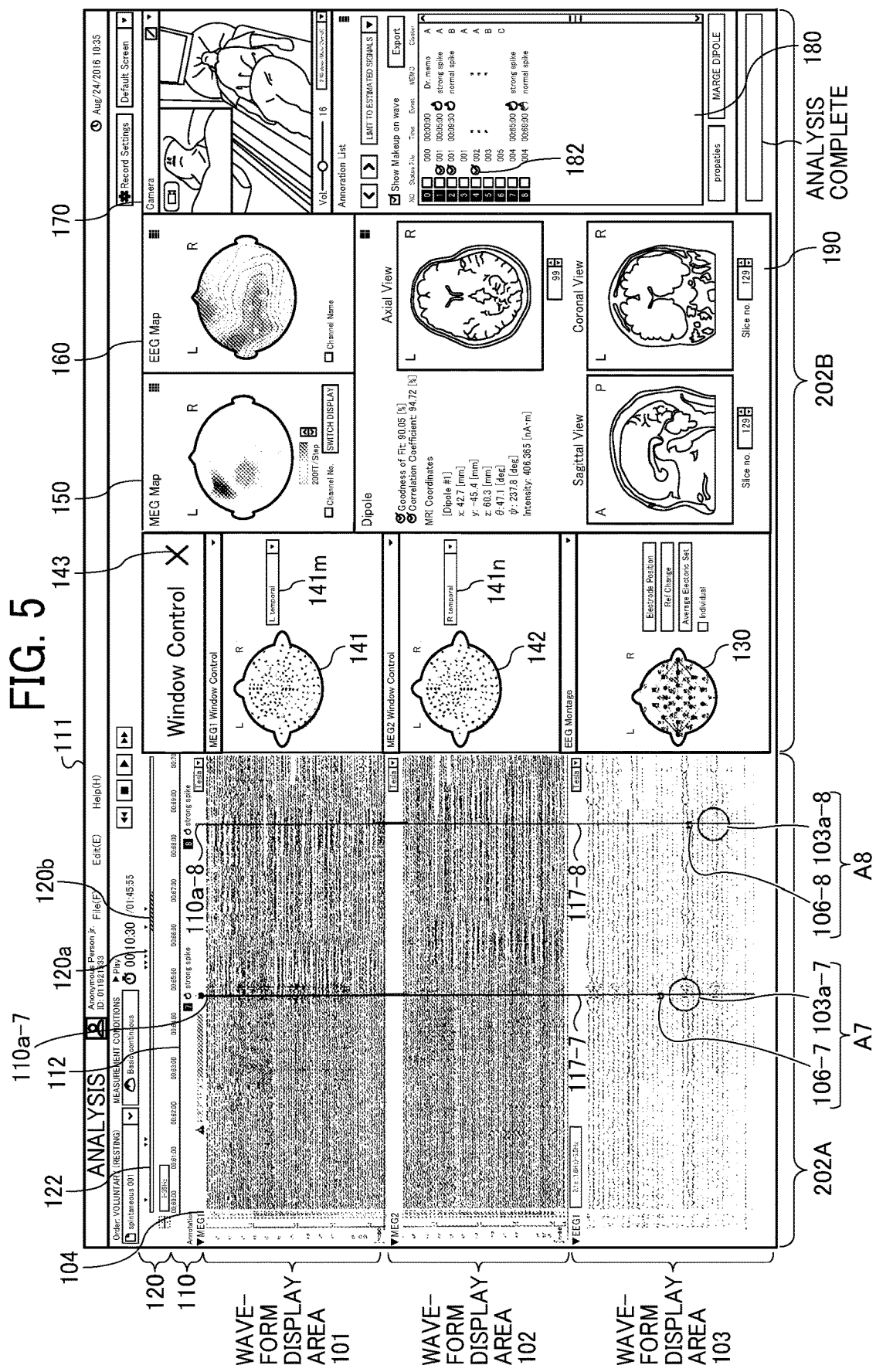
FIG. 5 is a diagram illustrating an analyzing screen according to an embodiment of the present disclosure.

FIG. 5 is a diagram illustrating a screen of the information processing device 50 when analysis is being performed, according to the present embodiment.

The analysis screen is displayed when the "analysis" button on the starting screen 204 as illustrated in FIG. 2 is selected. In the analyzing screen, biomedical data that indicates the changes over time in at least one biomedical signal of a test subject obtained in the measurement (i.e., in the present embodiment, the magnetic signals obtained through a plurality of magnetic sensors from the right side of the head of a subject, the magnetic signals obtained through a plurality of magnetic sensors from the left side of the head of a subject, and the electrical signals obtained through electrodes for measuring the brain wave of the subject) is associated with at least one annotation that is input and added to the biomedical data during the measurement. In the present embodiment, the display controller 251 of the information processing device 50 controls a display (i.e., a display 28 as will be described later in detail) to display the analyzing screen. In the present embodiment as illustrated in FIG. 5, the analyzing screen includes an area 202A in which the waveform that indicates the changes over time in three recorded biomedical signals (such waveforms correspond to biomedical data) is displayed together with annotations, and an area 202B in which analyzed data is displayed. In the present embodiment, the waveform that indicates the changes over time in three recorded biomedical signals is displayed on the analyzing screen. However, no limitation is intended thereby. For example, there are some cases in which input signals of a stimulator that causes a stimulus to be given to a test subject are displayed. For this reason, the number of signals is not limited to three. The area 202A in which the recorded signal waveform and the annotation data are displayed is arranged on the left side of the screen when viewed from the technician, and the area 202B on which analyzed data is displayed is arranged on the right side of the screen when viewed from the technician. As described above, it is desired that the area 202A and the area 202B be displayed simultaneously in parallel, because during the analysis the analyst can easily and efficiently check or finalize the analytical results in the area 202B by operating, for example, a mouse, while checking or selecting a signal waveform in the area 202A.

In the present embodiment, the waveforms of the magneto-encephalography (MEG) signals in the waveform display areas 101 and 102 are displayed above the screen of the waveform of the electrical signals in the waveform display area 103 of the area 202A. In the area 202B on the right side of the area 202A, the magneto-encephalogram distribution maps 141 and 142 are displayed on the topside of the screen area close to the area 202A, and the brain-wave distribution map 130 is displayed under the magneto-encephalogram distribution map 142. Accordingly, the analyst can train his/her line of sight from the waveform of the electrical signals in the waveform display area 103, to the waveform of the magneto-encephalography (MEG) signals in the waveform display areas 101 and 102, and then to the magneto-encephalogram distribution maps 141 and 142 and the brain-wave distribution map 130 (in a clockwise direction in the present embodiment). Due to this configuration, the analyst (or the technician) can train his/her line of sight efficiently, and thus the efficiency of analysis can improve. In the above description, the line of sight is moved in a clockwise direction. However, no limitation is intended thereby.

Next to the magneto-encephalogram distribution map 141, the waveforms that are output from multiple sensors indicated by each sensor image are displayed in the waveform display area 101. In other words, the waveform display area 101 and the magneto-encephalogram distribution map 141 are displayed parallel to each other in the direction of waveform propagation. In a similar manner, the waveform display area 102 and the magneto-encephalogram distribution map 142 as well as the waveform display area 103 and the brain-wave distribution map 130 are also displayed next to each other and parallel to each other in the direction of waveform propagation.

The area 202A includes the time-indicating area 110 in which the time data of the measurement is displayed in the horizontal direction (i.e., the first direction) of the screen, a time-slot display area 120, and the waveform display areas 101 to 103 in which the recorded signal waveforms are displayed in parallel on a type-of-signal by type-of-signal basis in the vertical direction (i.e., the second direction) of the screen.

In time-indicating area 110, the time axis 112 that indicates the lapse of time during the recording, and annotations 110*a*-7 and 110*a*-8 that are added along the time axis 112 are displayed.

In the time-slot display area 120, the time axis 122 that indicates the entire lapse of time during the recording is displayed. Moreover, a pointer mark 120*a* that indicates the point in time at which an annotation is given and a time zone 120*b* indicating a time zone in which the signal waveforms that are currently displayed in the waveform display areas 101 to 103 are recorded are displayed along the time axis 122. Due to such display, the analyst can intuitively figure out at what time slot of the measurement and recording were the signal waveforms that are being analyzed are obtained.

For example, the analyst may drag a time zone 120*b* on the bar of the time axis 122 after opening the analyzing screen. By so doing, the signal waveform in a desired time zone can be displayed in the waveform display areas 101 to 103. Alternatively, as will be described later in detail, the analyst may select a desired annotation from the annotation list 180. Due to this configuration, the display controller 251 can display the above-selected annotation and the signal waveform around the selected annotation in the waveform display areas 101 to 103.

In the waveform display areas 101 to 103, annotations A7 and A8 that are added to the signal waveforms during the recording are displayed. Marks 103a-7 and 103a-8 are highlighted, and the corresponding attribute icons 106-7 and 106-8 are displayed near the marks 103a-7 and 103a-8. Moreover, vertical lines 117-7 and 117-8 that indicate the points in time of the marks 103a-7 and 103a-8 are displayed. As the lines 117 are displayed, for example, when an annotation is given in association with the selection of a certain portion of the waveform display area 103, the analyst can visually recognize the results of selection easily also in the other signal display areas, i.e., the waveform display areas 101 and 102. The lines 117-7 and 117-8 enable easy visual recognition of the annotation data. In this sense, the lines 117-7 and 117-8 may be considered to be annotation data, and may be referred to as annotation lines.

In the analyzing screen illustrated in FIG. 5, the magneto-encephalogram distribution maps 141 and 142 that correspond to the signal waveforms displayed in the waveform display areas 101 and 102, respectively, and the brain-wave distribution map 130 that correspond to the signal waveform displayed in the waveform display area 103 are displayed. Moreover, an isomagnetic field 150 of a magneto-encephalograph (MEG), a map area 160 of an electro-encephalograph (EEG), and a display window 190 for the tomographic images of the brain of a subject obtained in the magnetic resonance imaging (MRI) are displayed in the analyzing screen illustrated in FIG. 5. In the isomagnetic field 150, a source area and a sink area of the magnetic field are displayed with coloring, and thus the direction in which the electric current flows can visually be identified. The isomagnetic field 150 and the map area 160 are the data obtained after the measurement is completed, and the MRI tomographic images are separately obtained in an examination.

In the monitoring window 170, the live image of the subject during the measurement is displayed in synchronization with the time at which the signal waveforms in the waveform display areas 101 to 103 are obtained. The analyst can analyze the signal waveforms while viewing the monitoring window 170 to check the state of the subject.

The annotation list 180 includes all the annotations added in the measurement recording.

Unlike the measurement and recording screen, the analyst checks the signal waveform of annotated portion, and an estimation completion mark 182 is displayed for each of the annotations whose signal sources are finally estimated.

Figure 6:
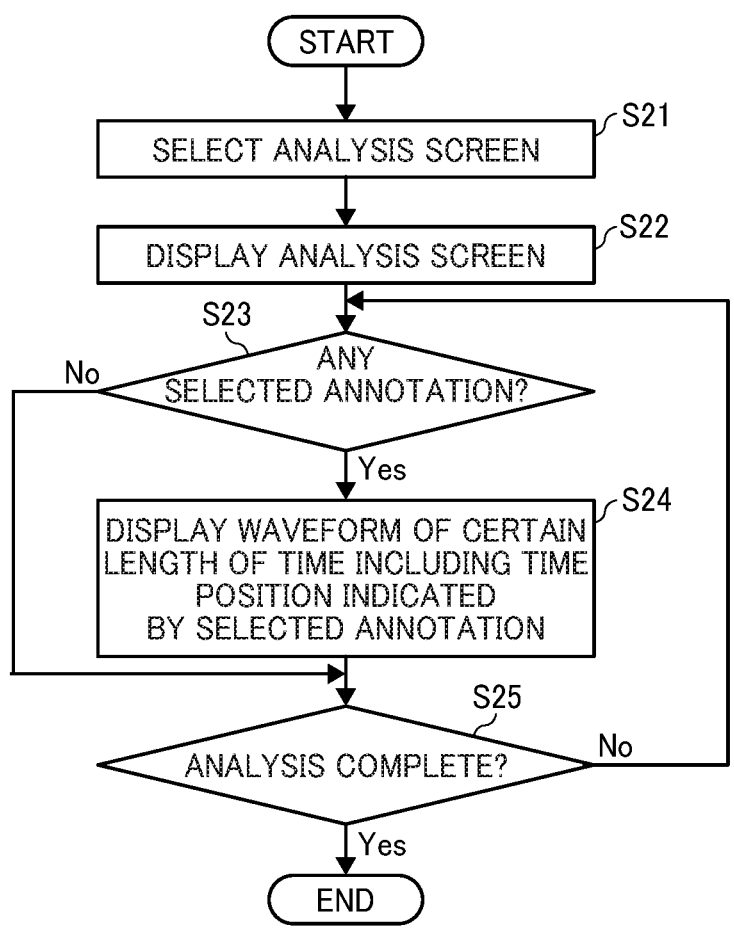
FIG. 6 is a flowchart of the operations performed by an information processing device during the analysis, according to an embodiment of the present disclosure.

FIG. 6 is a flowchart of display information processing performed by the information processing device 50 in a stage of analysis, according to the present embodiment.

When "analysis" is selected on the starting screen 204 as illustrated in FIG. 2, the acceptance unit 52 of the information processing device 50 accepts the selection (step S21). Accordingly, the analysis starts, and the display controller 251 controls the display to display an analyzing screen (step S22). The initial analyzing screen may be a blank screen on which no signal waveform is displayed, or may display signal waveforms in a predetermined time range at the head or tail end of the recording. Once an analyzing screen is displayed, the determining unit 55 determines whether a certain annotation is selected (a step S23). The selection of an annotation may be the selection of a certain annotation number or a certain row in the annotation list 180, or may be the designation of a point in time by operating the time zone 120b along the time axis 122 of time-slot display area 120. When an annotation is selected (YES in the step S23), the display controller 251 controls the display to display the signal wavelength of a certain length of time including the point in time indicated by the selected annotation (S24). After that, until an analysis termination command is input (YES in a step S25), the processes in the steps S23 and S24 are repeated.

Due to the display processing as described above, information display with high-level visual recognizability and operability is achieved.

First Embodiment

FIG. 7A, FIG. 7B, FIG. 7C, and FIG. 7D are diagrams each illustrating the magneto-encephalogram distribution map 141 according to a first embodiment of the present disclosure.

The magneto-encephalogram distribution map 141 indicates the relative positions of the magnetic sensors with reference to the head of a test subject. The magneto-encephalogram distribution map 141 includes a figure 141-1 of the external shape of a head and a plurality of sensors 141-2. The sensor imagery consists of round small dots indicating the relative positions of the sensors that are the sources of the waveforms displayed in the waveform display area 101.

In the figure 141-1 of the external shape of the head, a triangular part indicating the nose of the test subject is displayed on the topside, and a pair of small semicircular parts that project to the right and left sides indicates the ears of the test subject. Assuming that the nose indicates the front side, L and R indicate the left side and the right side, respectively. The sensors 141-2 indicate the arrangement of the magnetic sensors for measuring brain magnetism that are disposed on the inner surface of the hollow 31 of the Dewar 30 (see FIG. 1), and each dot depicted in FIG. 7A indicates a magnetic sensor.

When the waveforms that are to be displayed in the waveform display area 101 are to be localized to the waveforms of a specific site of the head, the person who records the data or the analyst selects desired ones of the multiple pieces of sensor imagery displayed in the magneto-encephalogram distribution map 141, using, for example, a mouse.

As an example of a selection method, as illustrated in FIG. 7A, the technician or the analyst encircles the desired ones of the multiple magnetic sensors, using an operation unit such as a mouse, in order to specify a selected region 141a-1 including a plurality of pieces of sensor imagery. Accordingly, the acceptance unit 52 accepts the designation of magnetic sensors, and as illustrated in FIG. 7B, the display controller 251 controls the display to display single-region data 141-3 indicating the designated region including the position information of a plurality of magnetic sensors. Note that the region data 141-3 appears as if the selected region 141a-1 as illustrated in FIG. 7A is filled in. As described above, the sensor imagery of magnetic sensors can collectively be selected as the technician or the analyst designates the selected region 141a-1. In this configuration, the magneto-encephalogram distribution map 141 serves as both a "position representation area" indicating the position of each of a group of sensors that detect the biomedical signals of a test subject and a "selection acceptance area" that accepts the selection of a plurality of positions of a plurality of desired sensors among the group of sensors.

As another example of a selection method, as illustrated in FIG. 7C, the region of magnetic sensors may be selected from a list. Once the technician or the analyst touches or presses a list display key 141m-1 in a menu 141m, the acceptance unit 52 accepts the touching or pressing, and the display controller 251 controls the display to display a pull-down menu 141m-2 as illustrated in FIG. 7C. In the pull-down menu 141m-2, options of the regions of magnetic sensors, which are registered in advance, are displayed. In such a configuration, once the technician or the analyst selects a desired option from the pull-down menu 141m-2 the acceptance unit 52 accepts the selection of a plurality of positions, and the display controller 251 controls the display to display region data 141-4 as illustrated in FIG. 7D. In this configuration, the magneto-encephalogram distribution map 141 serves as a "position representation area" indicating the position of each of a group of sensors that detect the biomedical signals of a test subject, and the pull-down menu 141m-2 serves as a "selection acceptance area" that accepts the selection of a plurality of positions of a plurality of desired sensors among the group of sensors.

Regarding the configuration where the sensors from which waveforms are output are selected as above by designating a region by a mouse or through a pull-down menu, the same applies to the magneto-encephalogram distribution map 142. The sensor imagery is an example of position information, and the position information includes, for example, a rectangular or triangular icon or an icon shaped like a sensor.

Figure 18:
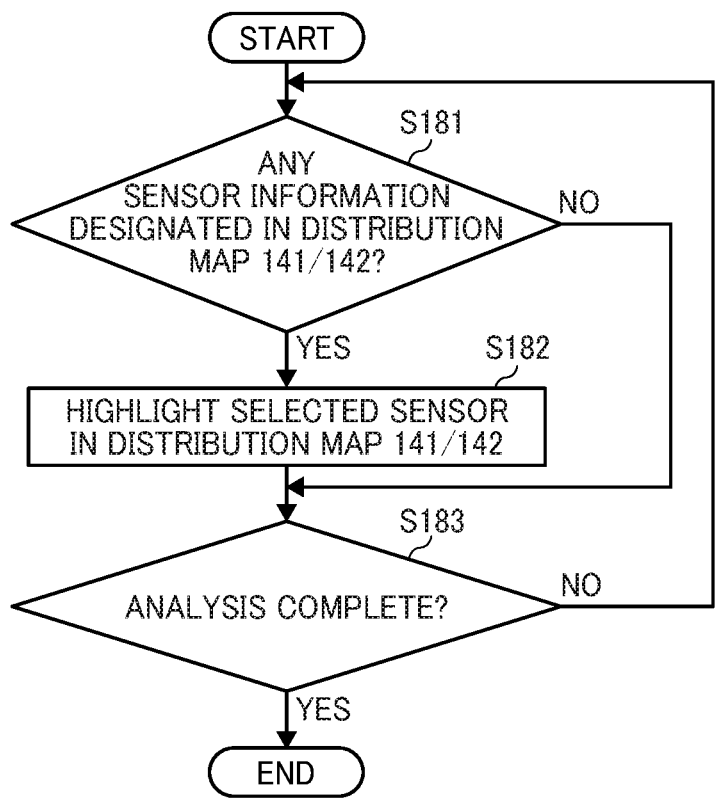
FIG. 18 is a flowchart of displaying operation performed on a magneto-encephalogram distribution map according to an embodiment of the present disclosure.

For example, FIG. 18 is a flowchart of displaying operation performed on a magneto-encephalogram distribution map according to an embodiment of the present disclosure.

The determining unit 55 determines whether the selection of desired sensors in the magneto-encephalogram distribution map 141 as illustrated in FIG. 3 or FIG. 5 is accepted by the acceptance unit 52 (step S181). The selection of sensors is performed by the person who records the data or the analyst. Then, when the determining unit 55 determines that the selection is accepted (YES in the step S181), the display controller 251 highlights the region of sensors accepted by the acceptance unit 52 in the magneto-encephalogram distribution map 141 (step S182). Such highlighting is as illustrated in FIG. 7B or FIG. 7B, or as illustrated in FIG. 8A, FIG. 8B, FIG. 8C, and FIG. 8D as will be described later in detail.

Subsequently, when a region of magnetic sensors is further selected (NO in a step S183), the analyzing processes in the steps S181 and S182 are repeated. On the other hand, when the processes in the steps S181 and S182 are not performed and the analyzing processes are to be terminated (YES in the step S183), the present process is terminated. Note that the processes are performed for the magneto-encephalogram distribution map 142 in a similar manner to the above. Moreover, the term "analysis" in the step S183 may be replaced with "measurement."

As described above, according to the present embodiment, the region of the selected magnetic sensors is filled with a brighter or darker color, and thus the distinguishability of the boundary between the region of the selected magnetic sensors and the region of the unselected magnetic sensors improves. Further, the region of the selected magnetic sensors can visually be recognized instantly.

First Modification of First Embodiment

Figure 8A:
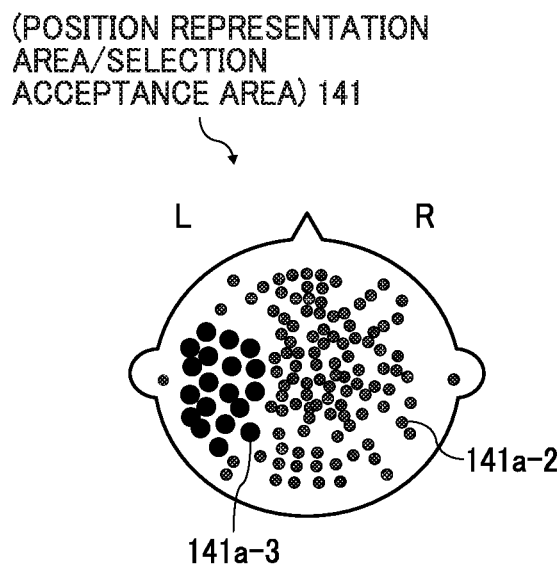
FIG. 8A, FIG. 8B, FIG. 8C, and FIG. 8D are diagrams each illustrating a modification of a magneto-encephalogram distribution map according to an embodiment of the present disclosure.

Next, a first modification of the first embodiment of the present disclosure is described. In FIG. 8A, the selected dots of the sensors 141a-2 are displayed as sensor imagery 141a-3 upon being enlarged and filled with a brighter or darker color. In this respect, FIG. 8A is different from FIG. 7A, FIG. 7B, FIG. 7C, and FIG. 7D. In the first modification, in a similar manner to FIG. 7A, FIG. 7B, FIG. 7C, and FIG. 7D, the technician or the analyst selects a desired region of magnetic sensors. Once a desired region of magnetic sensors is selected, the size of the dots of the sensors 141-2 in the selected region is displayed larger than the sensors in the unselected region. As the intervals at which the sensors are displayed in the selected region become narrower compared with when the selection was not yet made, an effect similar to that of FIG. 7A, FIG. 7B, FIG. 7C, and FIG. 7D can be achieved. Note also that the size of the dots of the selected sensors may be so large as to overlap with the neighboring sensors. In such a configuration, it is desired that the overlapping sensors be regarded as a group of collectively selected sensors, and that an interval be placed between the overlapping sensors and the unselected sensors.

Second Modification of First Embodiment

Figure 8B:
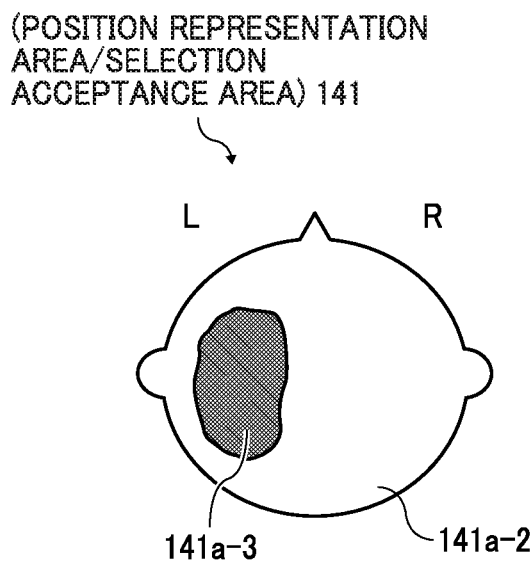
Figure 8C:
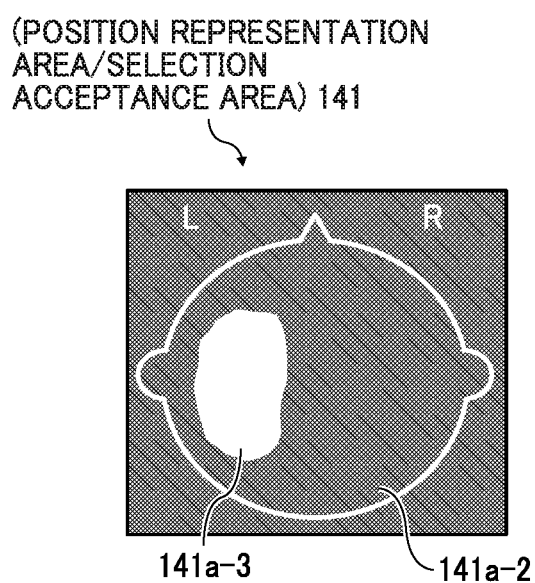
Figure 8D:
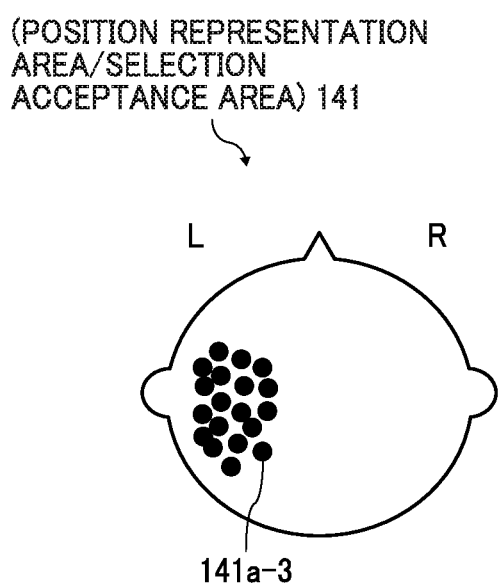

Next, a second modification of the first embodiment of the present disclosure is described. FIG. 8B is different from FIG. 7A, FIG. 7B, FIG. 7C, and FIG. 7D in that the unselected sensors 141-2 are hidden from view. FIG. 8D is different from FIG. 8A in that the unselected sensors 141-2 are hidden from view.

In the second modification, in a similar manner to FIG. 7A, FIG. 7B, FIG. 7C, and FIG. 7D, the technician or the analyst selects a desired region of magnetic sensors. In the case of FIG. 8B, once a desired region of magnetic sensors is selected, the selected region is filled with a brighter or darker color, and the sensors 141-2 in the unselected region are hidden from view. In the case of FIG. 8D, once a desired region of magnetic sensors is selected, the size of the dots of the sensors 141-2 in the selected region is displayed larger than the sensors in the unselected region, and the sensors 141-2 in the unselected region are hidden from view.

When the sensors 141-2 are densely packed, the unselected group of sensors may be misidentified as if the unselected group of sensors are shaded or filled with a brighter or darker color depending on environmental conditions. By contrast, according to the second modification of the present embodiment, the unselected group of sensors are hidden from view, and thus the selected group of sensors can visually be recognized with even greater reliability.

Third Modification of First Embodiment

Next, a third modification of the first embodiment of the present disclosure is described. FIG. 8C is different from FIG. 8B in that the background color of the region of the unselected sensors 141-2 are made pale or close to the background color of the distribution map. In this configuration, the region data of the selected sensors 141a-3 is white or a color distinguishable from the background color of the distribution map. In the third modification of the present embodiment, the dots that indicate the selected sensors may further be displayed, or may be hidden from view as illustrated in FIG. 8C. By displaying the region data of the selected sensors 141a-3 in a distinguishable manner from the background color, the recognizability further improves. Note also that the configuration of the present modification can be applied to the configuration of FIG. 8A.

Fourth Modification of First Embodiment

Next, a fourth modification of the first embodiment of the present disclosure is described. In FIG. 7B and FIG. 8B, the color of the selected group of sensors (141a-1, 141a-3) and the color of the unselected group of sensors (141-2, 141a-2) may be differentiated from each other. For example, compared with the color of the unselected group of sensors (141-2, 141a-2), the color of the selected group of sensors (141a-1, 141a-3) may be made distinguishable or highlighted. Due to this configuration, the visual recognizability of the selected group of sensors further improves.

Second Embodiment

Next, a second embodiment of the present disclosure is described.

Figure 9:
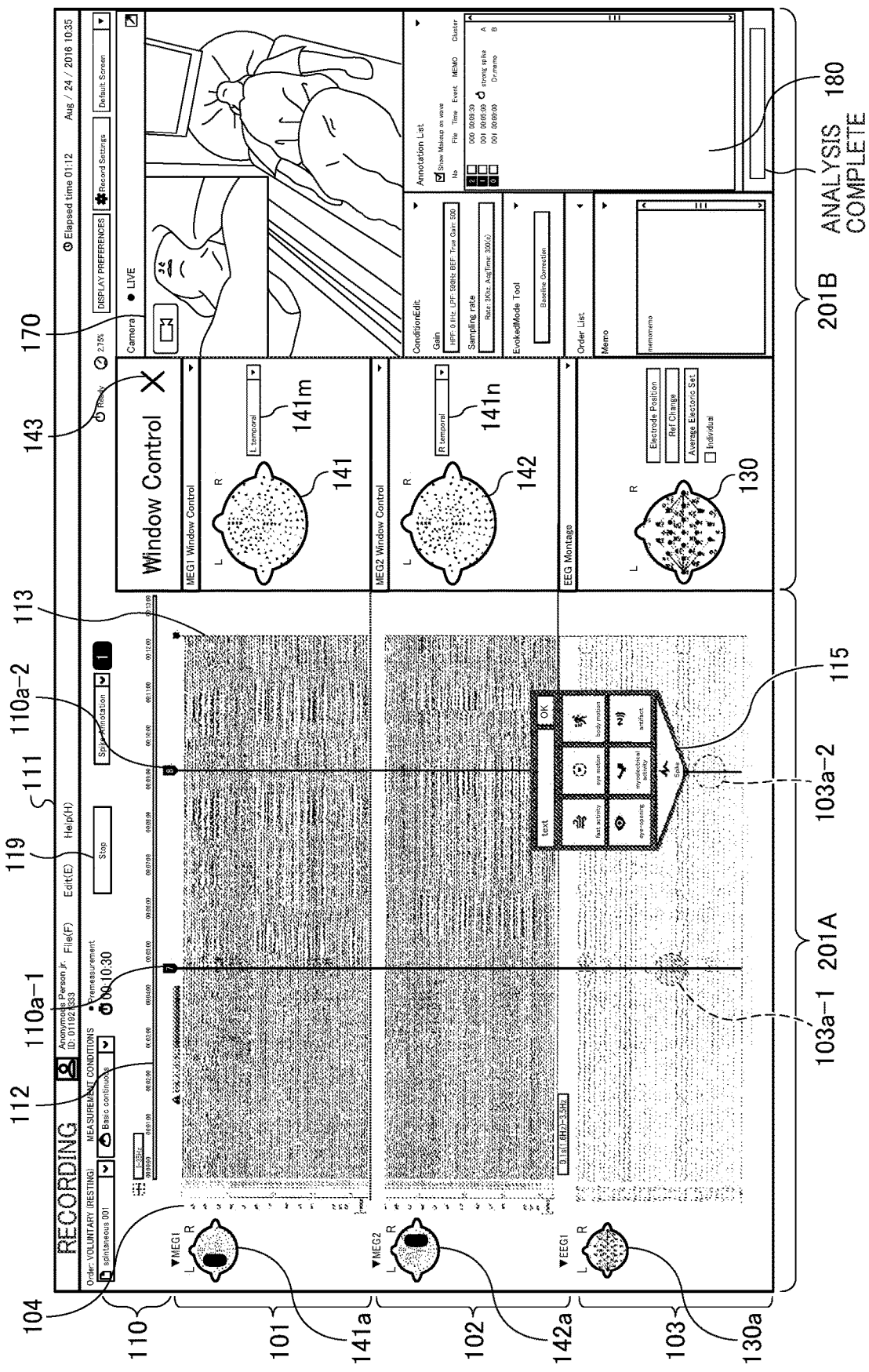
FIG. 9 is a diagram illustrating a measurement and recording screen according to an embodiment of the present disclosure.

FIG. 9 is a diagram illustrating a recording screen according to a second embodiment of the present disclosure, which corresponds to the measurement and recording screen illustrated in FIG. 3.

Figure 10:
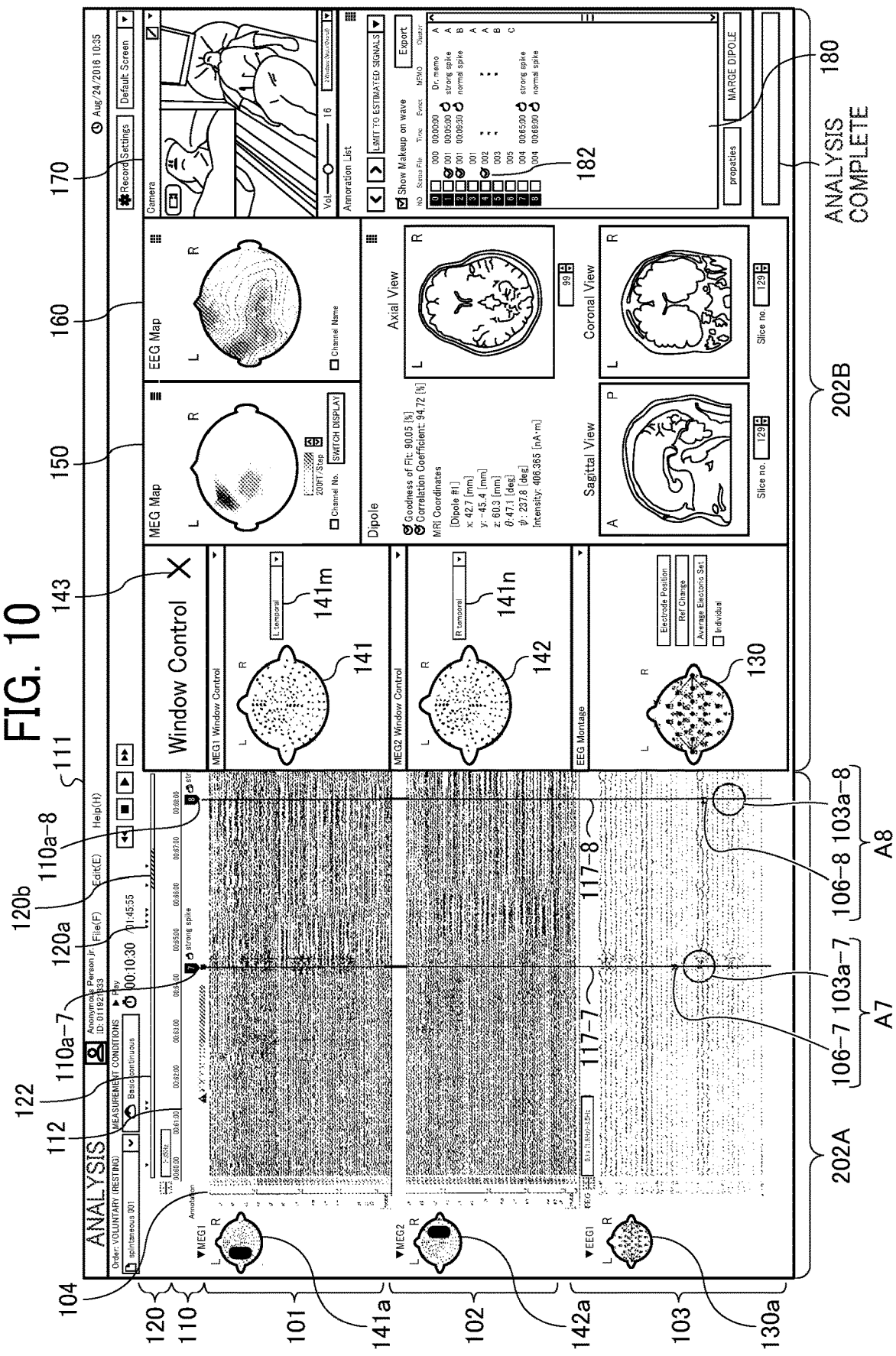
FIG. 10 is a diagram illustrating an analyzing screen according to an embodiment of the present disclosure.

FIG. 10 is a diagram illustrating an analyzing screen according to the second embodiment of the present disclosure, which corresponds to the analyzing screen illustrated in FIG. 5.

Next to the channel axis 104 illustrated in FIG. 9 and FIG. 10, downsized images 141a, 142a, and 130a of the magneto-encephalogram distribution maps 141 and 142 and the brain-wave distribution map 130 are displayed. As illustrated in FIG. 11A, the magneto-encephalogram distribution map 141 consist of the figure 141-1 of the external shape of the head and the multiple sensors 141-2. In the figure 141-1 of the external shape of the head, a triangular part indicating the nose of the test subject is displayed on the topside, and a pair of small semicircular parts that project to the right and left sides indicate the ears of the test subject. Assuming that the nose indicates the front side, L and R indicate the left side and the right side, respectively. The sensors 141-2 indicate the arrangement of the magnetic sensors for measuring brain magnetism that are disposed on the inner surface of the hollow 31 of the Dewar 30 (see FIG. 1), and each dot depicted in FIG. 7A indicates a magnetic sensor.

As illustrated in FIG. 7A or FIG. 7C, once the technician or the analyst narrows down the sensors whose waveforms are to be displayed in the waveform display area 101, the selected dots of the sensors 141-2 are displayed in a color distinguishable from the unselected dots of the sensor imagery on the magneto-encephalogram distribution map 141 as illustrated in FIG. 11A. By contrast, in the downsized image 141a as illustrated in FIG. 11B, an area around the region data including the selected sensors 141a-3 is filled with a brighter or darker color. A figure 141a-1 of the external shape of the head and a plurality of sensors 141a-2 in the downsized image 141a are obtained by downsizing the magneto-encephalogram distribution map 141.

As is apparent from the measurement and recording screen as illustrated FIG. 9 and the analyzing screen as illustrated in FIG. 10, more sensors are displayed in the magneto-encephalogram distribution map 141. For this reason, if the distribution map is downsized just as it is, the spaces between those sensors shrink, and the visual recognizability of those sensors (in particular, the recognizability of what sensors are selected) is poor. By contrast, in the present embodiment, the display format of the downsized image (magneto-encephalogram distribution map) 141a is made different from the display format of the magneto-encephalogram distribution map 141. Due to this configuration, even when the downsized image is displayed in detail, the visual recognizability of the downsized image improves.

The numbers given to the sensors in the sensor imagery selected in the magneto-encephalogram distribution map may be displayed along the channel axis 104 displayed on the measurement and recording screen as illustrated FIG. 9 and the analyzing screen as illustrated in FIG. 10. However, with such numbers, it is difficult to recognize what group of sensors in the figure of the external shape of the head is indicated. By contrast, the downsized image 141a is displayed next to (or near) the channel axis 104 in the present embodiment. Due to this configuration, it becomes easy to visually recognize what group of sensors in the figure of the external shape of the head is indicated by the sensors indicated along the channel axis 104.

By way of example, the downsized image 141a is described with reference to FIG. 11A and FIG. 11B. However, the configuration as illustrated in FIG. 11A and FIG. 11B may be applied to the downsized image (magneto-encephalogram distribution map) 142a as illustrated in FIG. 9 and FIG. 10. In the above description, the figure of the external shape of a head as illustrated in FIG. 11B is explained as a miniature of the figure of the external shape of a head as illustrated in FIG. 11A. However, no limitation is indicated thereby, and these figures of the external shape of the head may be different from each other. For example, the figure of FIG. 11B may appear similar to any one of the figures of FIG. 12C, FIG. 12D, and FIG. 12E.

Figure 19:
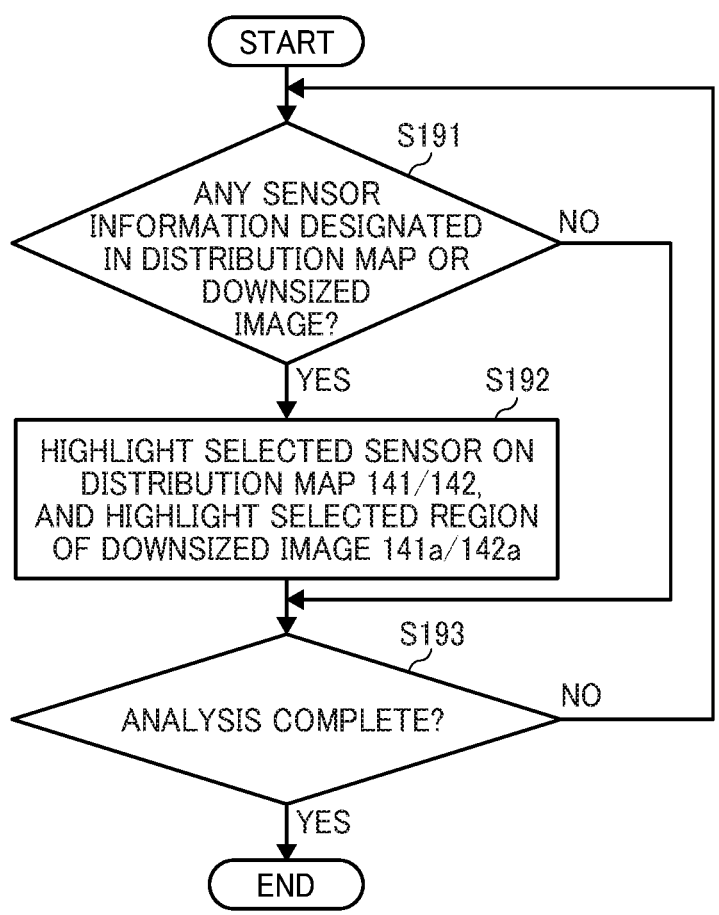
FIG. 19 is a first flowchart of displaying operation performed on a magneto-encephalogram distribution map and a downsized image, according to an embodiment of the present disclosure.

FIG. 19 is a first flowchart of a displaying operation performed on the magneto-encephalogram distribution map 141 and the downsized image 141a, according to the present embodiment.

The determining unit 55 determines whether the selection of desired sensors in the magneto-encephalogram distribution map 141 and the downsized image 141a as illustrated in FIG. 9 or FIG. 10 is accepted by the acceptance unit 52 (step S191). The selection of sensors is performed by the person who records the data or the analyst. Then, when the determining unit 55 determines that the selection is accepted (YES in the step S191), the display controller 251 highlights the region of sensors accepted by the acceptance unit 52 in the magneto-encephalogram distribution map 141, and highlights the region of sensors accepted by the acceptance unit 52 also in the downsized image (magneto-encephalogram distribution map) 141a (step S192). Subsequently, when a region of magnetic sensors is further selected or unselected (NO in a step S193), the analyzing processes in the steps S191 and S192 are repeated. On the other hand, when the processes in the steps S191 and S192 are not performed and the analyzing processes are to be terminated (YES in the step S193), the present process is terminated. Note that the processes are performed for the magneto-encephalogram distribution map 142 and the downsized image 142a in a similar manner to the above. Moreover, the term "analysis" in the step S193 may be replaced with "measurement."

First Modification of Second Embodiment

Next, a first modification of the second embodiment of the present disclosure is described. When the sensors 141a-2 are densely packed and the image is downsized, the intervals between the sensors become narrower compared with a normal screen. Accordingly, the unselected group of sensors may be misidentified as if these sensors are shaded or filled with a brighter or darker color depending on environmental conditions. In order to avoid such a situation, the configurations as illustrated in FIG. 8B and FIG. 8C may be applied to the configurations of the downsized images 141a and 142a. Accordingly, the unselected group of sensors are hidden from view and the selected group of sensors 141a-3 can visually be recognized with even greater reliability.

As long as the sensors do not overlap when the image is downsized, the configurations as illustrated in FIG. 8A or FIG. 8D may be applied to the downsized images. In the case of the configuration as illustrated in FIG. 8D, the size of the dots of the sensors 141a-2 in the selected region is not necessarily compared with the size of the sensors in the unselected region. For example, it may be considered that the size of the dots of the sensors (sensor imagery) 141a-3 relative to the size of the figure 141-1 of the external shape of a head is larger than the size of the dots of the sensors 141-2 in FIG. 11A relative to the size of the figure 141-1 of the external shape of the head.

Further, the color of the selected group of sensors (141a-3) displayed in the downsized image and the color of the unselected group of sensors (141a-2) displayed in the downsized image may be differentiated from each other. For example, compared with the color of the unselected group of sensors (141a-3), the color of the selected group of sensors (141a-2) may be made distinguishable or highlighted. Due to this configuration, the visual recognizability of the selected group of sensors (141a-3) further improves.

Second Modification of Second Embodiment

Next, a second modification of the second embodiment of the present disclosure is described. If the corresponding downsized image is made to reflect all the region of the magnetic sensors (141d-2) specified by the technician or the analyst on the magneto-encephalogram distribution map 141, it is assumed that the work of executing a program increases. In order to avoid such a situation, some patterns of the regions of magnetic sensors to be displayed on a downsized image are stored in a memory (for example, a data storage unit 254 as will be described later) in advance. Then, the range specified by the technician or the analyst (141d-2 in FIG. 12A) is compared with the patterns stored in the memory to search for and extract a similar pattern, and the extracted pattern is displayed as the region data (of the sensors 141a-3 in FIG. 12B). In FIG. 12B, both the specified selected region 141d-2 and the sensors (region data) 141a-3 are illustrated to enable comparison. However, in actuality, only the sensors (region data) 141a-3 is displayed. For purposes of simplification of explanation, the figures in FIG. 12A and FIG. 12B are illustrated in the same size. In actuality, FIG. 12B illustrates a downsized image. Due to the configuration as described above, the work of executing a program can be reduced, and the operability further improves.

Alternatively, options of which similar pattern to select may be displayed upon comparing the selected region with the patterns stored in advance, and the technician or the analyst may be asked to select one of such options.

When options of which similar pattern to select are automatically displayed and when options of which similar pattern to select are displayed, a result of comparison (for example, a value of the degree of match) may be displayed near the downsized image.

Figure 21:
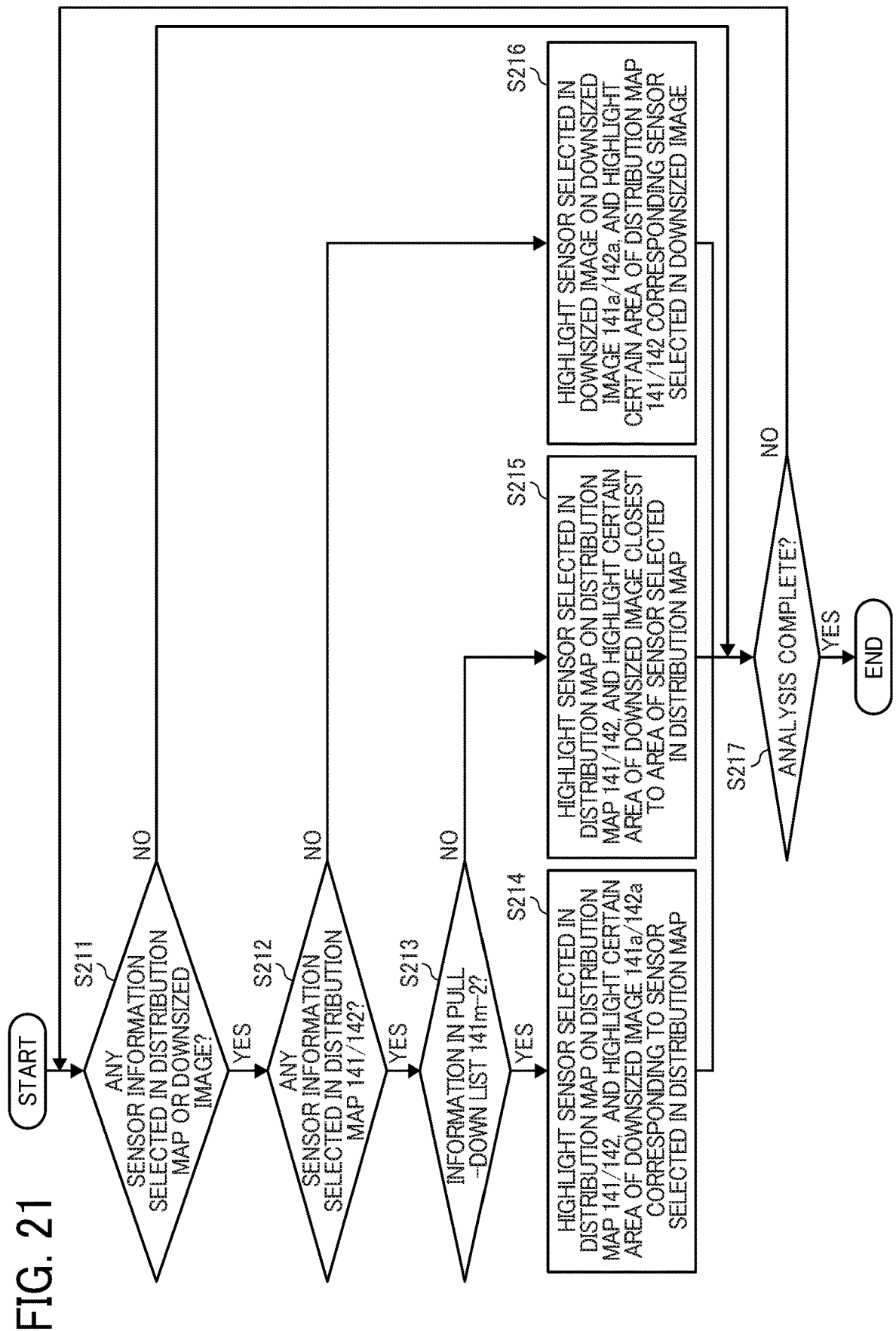
FIG. 21 is a third flowchart of displaying operation performed on a magneto-encephalogram distribution map and a downsized image, according to an embodiment of the present disclosure.

FIG. 21 is a third flowchart of a displaying operation performed on the magneto-encephalogram distribution map 141 and the downsized image 141a, according to the present embodiment.

The determining unit 55 determines whether the selection of desired magnetic sensors in the magneto-encephalogram distribution map 141 and the downsized image 141a as illustrated in FIG. 9 or FIG. 10 is accepted by the acceptance unit 52 (step S211). The selection of magnetic sensors is performed by the person who records the data or the analyst.

Then, when the determining unit 55 determines that the selection is accepted (YES in the step S211), the determining unit 55 further determines whether the selection of desired magnetic sensors in the magneto-encephalogram distribution map 141 as illustrated in FIG. 9 or FIG. 10 is accepted (step S212).

Subsequently, the determining unit 55 determines whether the desired magnetic sensors on the magneto-encephalogram distribution map have been selected by a person who records the data or an analyst from the pull-down menu 141m-2 illustrated in FIG. 7C (step S213). Then, when the determining unit 55 determines that the selection is made (YES in the step S213), the display controller 251 controls the display to display the selected dots of the sensors in a color distinguishable from the unselected dots, and controls the display to fill the same region of the downsized image 141a corresponding to the region selected in the magneto-encephalogram distribution map 141 (step S214).

On the other hand, when the selected region 141d-2 of desired sensors in the magneto-encephalogram distribution map is selected by a person who records the data or an analyst as in FIG. 12A (NO in the step S213) the display controller 251 controls the display to display the selected dots of the sensors in a color distinguishable from the unselected dots, and controls the display to display, as the downsized image 141a, the downsized image closest to the selected region selected on the magneto-encephalogram distribution map 141 (step S215).

When it is determined by the determining unit 55 that the magnetic sensors that are preset on the downsized image 141a by a person who records the data or an analyst have been selected (NO in the step S212) the display controller 251 highlights that region in the downsized image, and also controls the display to highlight the selected dots of the sensors in the magneto-encephalogram distribution map 141 in a color distinguishable from the unselected dots (step S216). When it is determined by the determining unit 55 that no sensor information has been selected in the step S211, the process proceeds to a step S217.

Subsequently, when a region of magnetic sensors is further selected (NO in a step S217), the analyzing processes in the steps S211 to S216 are repeated. On the other hand, when the processes in the steps S211 to S216 are not performed and the analyzing processes are to be terminated (YES in the step S217), the present process is terminated. Note that the processes are performed for the magneto-encephalogram distribution map 142 and the downsized image 142a in a similar manner to the above.

Third Modification of Second Embodiment

Next, a third modification of the second embodiment of the present disclosure is described. The downsized image 141a is displayed in order to enable a person who records the data or an analyst to visually identify the target region 141a-1 of the magnetic sensors selected on the magneto-encephalogram distribution map 141. For this reason, the figure of the external shape of a head may have any shape. In particular, it is satisfactory as long as the shape required to identify a desired region of magnetic sensors (for example, a triangular part indicating the nose of the test subject) is specified. For this reason, the display controller 251 may adjust the display to hide the ears of the test subject from view as illustrated in FIG. 12C, or may adjust the display to hide the external shape of the test subject from view except for just the nose and ears of the test subject as illustrated in FIG. 12D. Alternatively, the display controller 251 may adjust the display to hide the external shape of the test subject from view just except the nose of the test subject as illustrated in FIG. 12E.

Fourth Modification of Second Embodiment

Next, a fourth modification of the second embodiment of the present disclosure is described.

Figure 13:
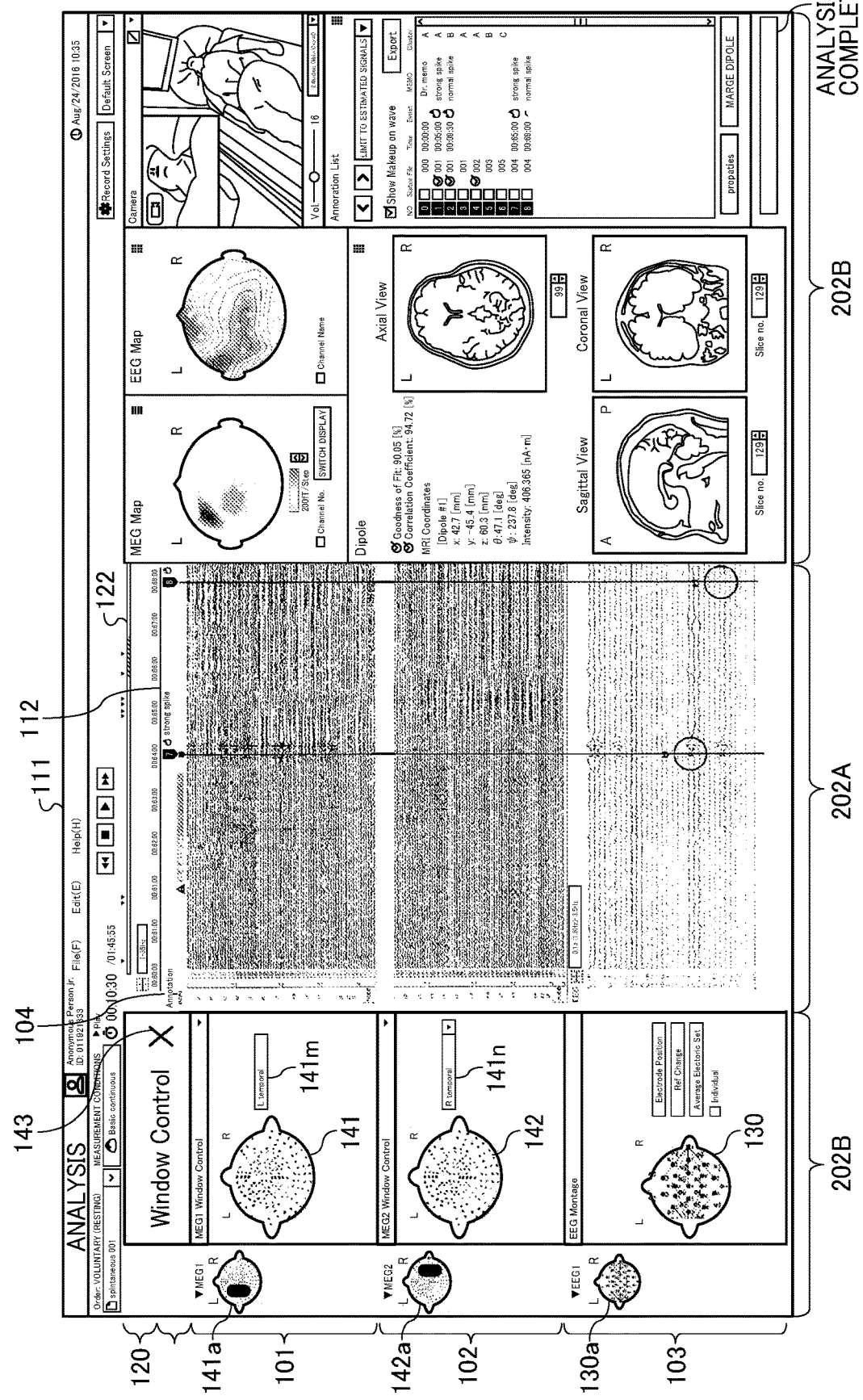
FIG. 13 is a diagram illustrating a first modification of a measurement and recording screen according to an embodiment of the present disclosure.

FIG. 13 is a diagram illustrating a modification of the analyzing screen in FIG. 10.

Note that the present modification of the second embodiment is applicable as a modification of the measurement and recording screen as illustrated in FIG. 9.

In FIG. 10, the magneto-encephalogram distribution maps 141 and 142 and the brain-wave distribution map 130 are displayed on the right side of the area 202A. Accordingly, the analyst can train his/her line of sight from the waveform of the electrical signals in the waveform display area 103, to the waveform of the magneto-encephalography (MEG) signals in the waveform display areas 101 and 102, and then to the magneto-encephalogram distribution maps 141 and 142 and the brain-wave distribution map 130 (in a clockwise direction in the present embodiment). Due to this configuration, the analyst (or the technician) can train his/her line of sight efficiently, and thus the efficiency of analysis can improve.

By contrast, in the present modification, the display controller 251 rearranges the display to display the magneto-encephalogram distribution maps 141 and 142 and the brain-wave distribution map 130 between the channel axis 104 and the downsized images 141a, 142a, and 130a. When the sensors to be displayed along the channel axis 104 are to be changed while the analyst (or the technician) is viewing the downsized images 141a, 142a, and 130a, the display controller 251 rearranges the display to di splay the magneto-encephalogram distribution maps 141 and 142 and the brain-wave distribution map 130 next to the downsized images 141a, 142a, and 130a. Due to this configuration, the range in which the line of vision moves can be shortened, and the workability or efficiency improves.

Fifth Modification of Second Embodiment

Next, a fifth modification of the second embodiment of the present disclosure is described. Regarding the waveforms displayed in the waveform display areas 101 to 103 of the measurement and recording screen as illustrated FIG. 9 and the analyzing screen as illustrated in FIG. 10, the workability or efficiency improves when the duration of time in which the waveforms are displayed is longer. In view of the above circumstances, in the present modification of the second embodiment, the display controller 251 is to be able to switch a state in which the magneto-encephalogram distribution maps 141 and 142 and the brain-wave distribution map 130 are displayed as illustrated in FIG. 9 and FIG. 10 to a state in which the magneto-encephalogram distribution maps 141 and 142 and the brain-wave distribution map 130 are hidden from view as illustrated in FIG. 14 and FIG. 15.

Figure 14:
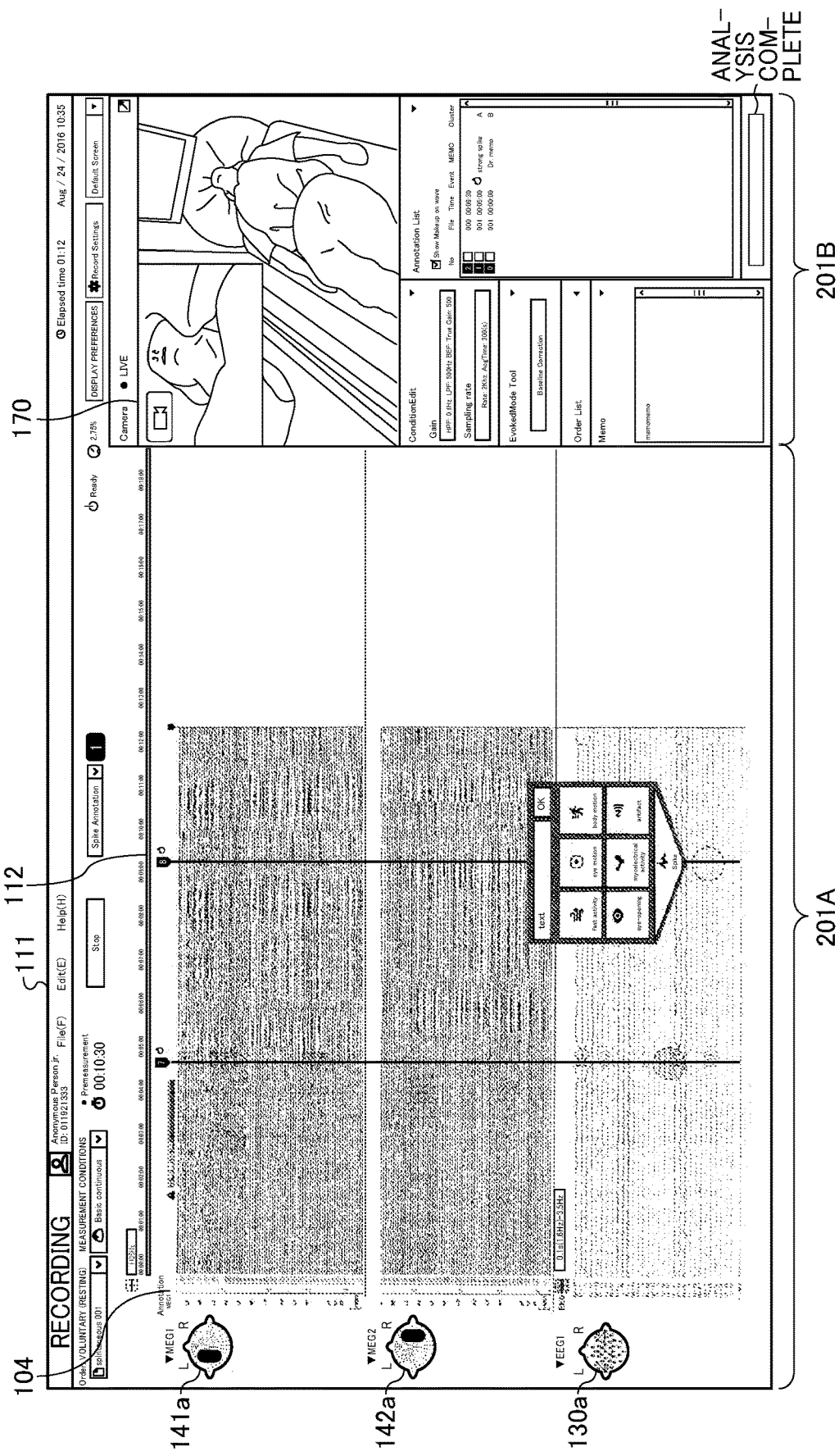
FIG. 14 is a diagram illustrating a second modification of a measurement and recording screen according to an embodiment of the present disclosure.

FIG. 14 is a diagram illustrating a measurement and recording screen according to the present modification of the second embodiment of the present disclosure.

Figure 15:
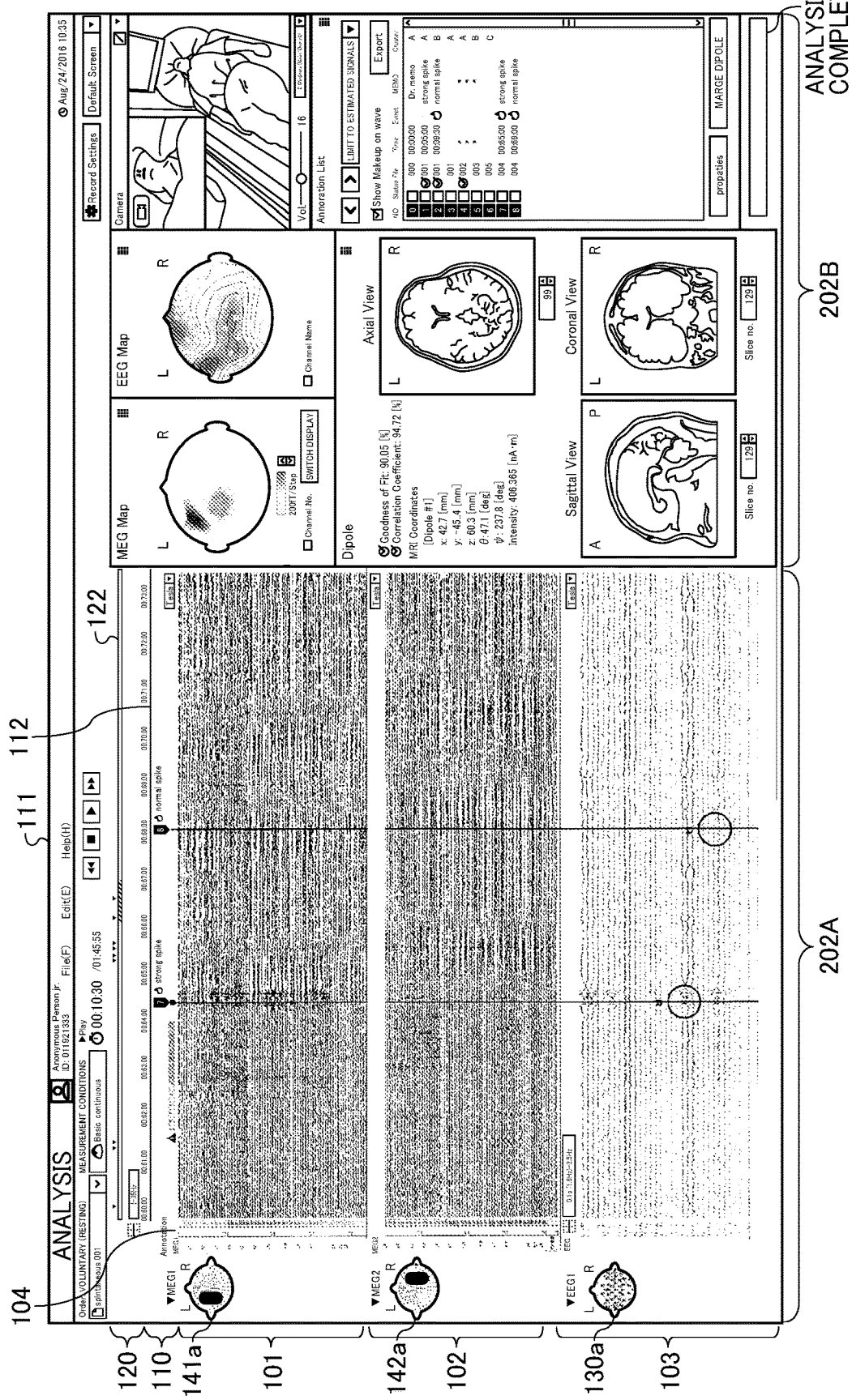
FIG. 15 is a diagram illustrating a modification of an analyzing screen according to an embodiment of the present disclosure.

FIG. 15 is a diagram illustrating an analyzing screen according to the present modification of the second embodiment of the present disclosure.

For example, when the technician touches or clicks a window close key 143 on the measurement and recording screen of FIG. 9 or when the analyst touches or clicks the window close key 143 on the analyzing screen of FIG. 10, the magneto-encephalogram distribution maps 141 and 142 and the brain-wave distribution map 130 are hidden from view, and the waveforms displayed in the waveform display areas 101 to 103 can be extended to the area where the magneto-encephalogram distribution maps were displayed.

On the other hand, when any of the downsized images 141a, 142a, and 130a is touched or clicked in a state as illustrated in the measurement and recording screen of FIG. 14 and the analyzing screen of FIG. 15, the magneto-encephalogram distribution maps 141 and 142 and the brain-wave distribution map 130 are displayed (see FIG. 9 and FIG. 10). When the screen is switched from the state of FIG. 14 (FIG. 15) to the state of FIG. 9 (FIG. 10), the waveforms to be displayed in the waveform display areas 101 to 103 are displayed in an area starting from the channel axis 104 of the waveforms displayed in the waveform display areas 101 to 103 of FIG. 14 (FIG. 15) and ending at the area corresponding to the width on the right and left sides of the magneto-encephalogram distribution maps 141 and 142 and the brain-wave distribution map 130. The time axis 112 is displayed in an area starting from the left end of the time displayed along the time axis 112 in FIG. 14 (FIG. 15) and ending at the area corresponding to the width on the right and left sides of the magneto-encephalogram distribution maps 141 and 142 and the brain-wave distribution map 130.

As described above, according to the present modification of the second embodiment, the waveforms of an even longer duration of time can be displayed in the waveform display areas 101 to 103. Accordingly, the workability or efficiency further improves. Note that the processes are performed for the magneto-encephalogram distribution map 142 and the downsized image 142a in a similar manner to the above. Note also that the configuration of the present modification can be applied to the example as illustrated in FIG. 13.

Sixth Modification of Second Embodiment

Figure 16A:
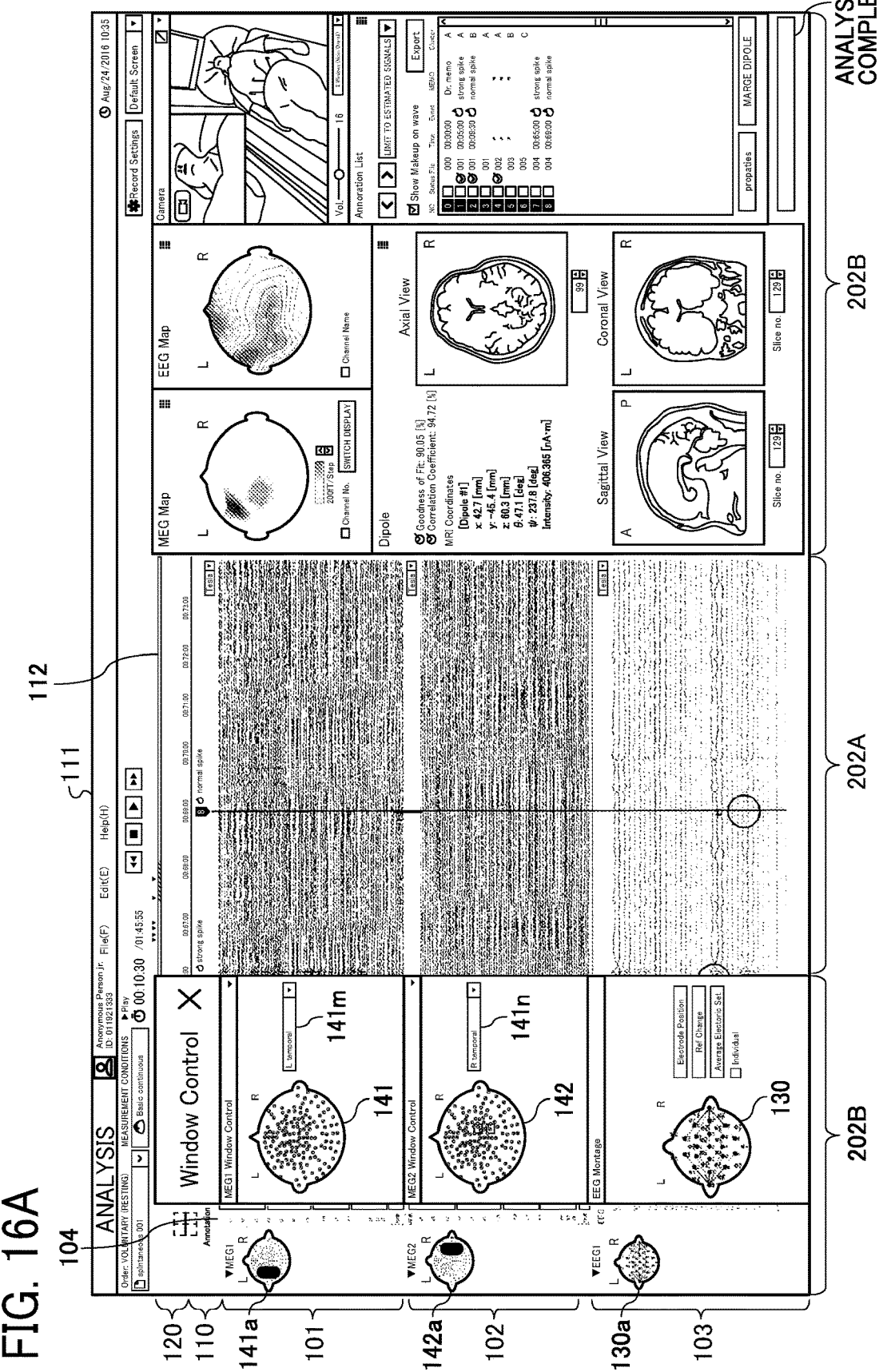
FIG. 16A is a diagram illustrating a first modification of an analyzing screen according to an embodiment of the present disclosure.

Next, a sixth modification of the second embodiment of the present disclosure is described. Once any of the downsized images 141a, 142a, and 130a is touched or clicked in a state as illustrated in the analyzing screen of FIG. 15, the magneto-encephalogram distribution maps 141 and 142 and the brain-wave distribution map 130 are displayed as illustrated in FIG. 16A. When the screen is switched from the state of FIG. 15 to the state of FIG. 16A, the waveforms displayed in the waveform display areas 101 to 103 remain unchanged from the display of FIG. 15. The magneto-encephalogram distribution maps 141 and 142 and the brain-wave distribution map 130 are superimposed on the waveforms so as not to hide the channel axis 104. In other words, the magneto-encephalogram distribution maps 141 and 142 and the brain-wave distribution map 130 are superimposed on older waveforms displayed in the waveform display areas 101 to 103.

As described above, in a similar manner to the fourth modification as illustrated in FIG. 13, the magneto-encephalogram distribution maps 141 and 142 and the brain-wave distribution map 130 are displayed near the downsized images 141a, 142a, and 130a. Due to this configuration, the range in which the line of vision moves can be shortened, and the workability or efficiency improves.

Figure 16B:
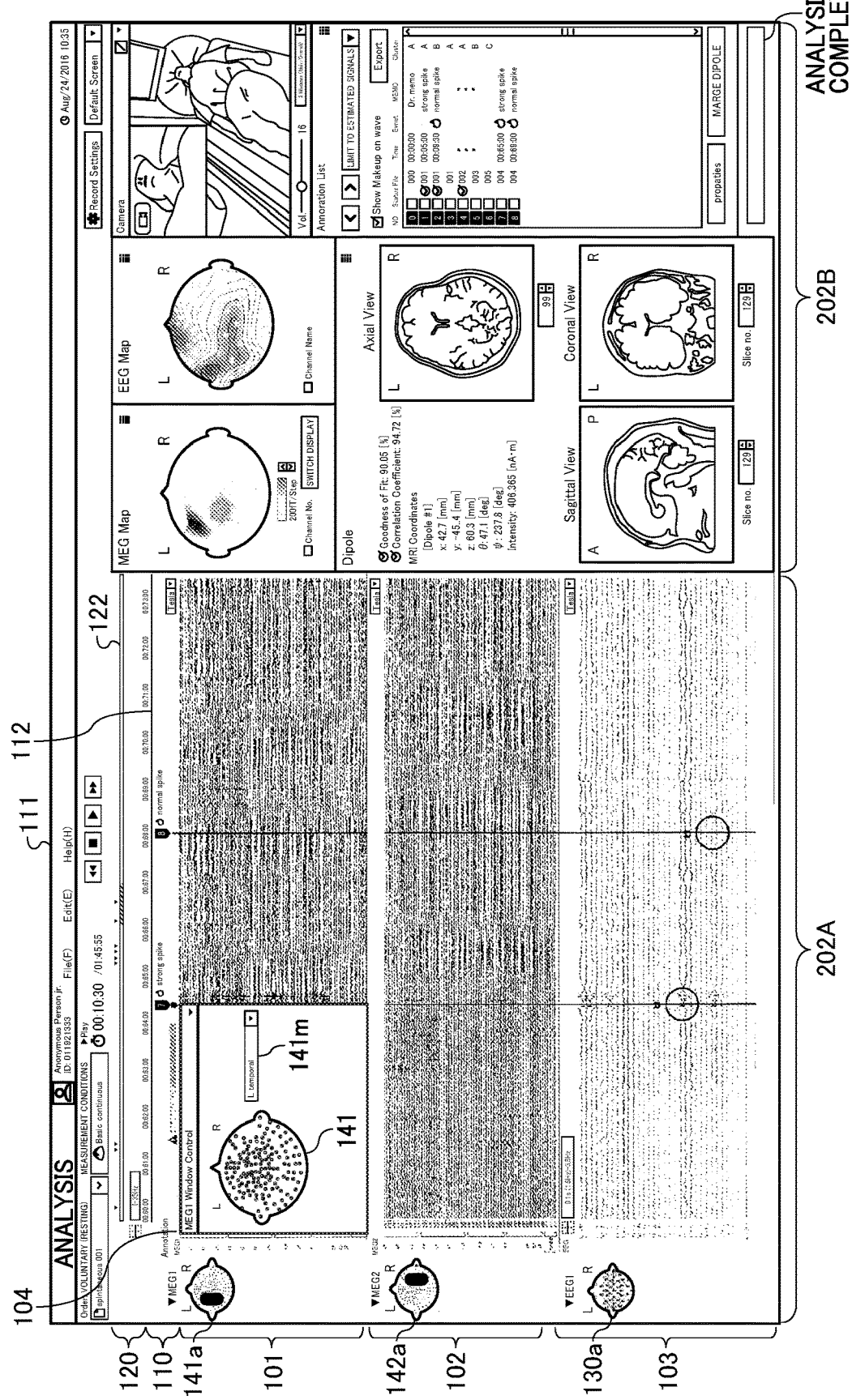
FIG. 16B is a diagram illustrating a second modification of an analyzing screen according to an embodiment of the present disclosure.

Alternatively, as illustrated in FIG. 16B, the magneto-encephalogram distribution map 141 142, or the brain-wave distribution map 130 that corresponds to the clicked or touched one of the downsized images 141a, 142a, and 130a may be displayed in the present modification of the second embodiment.

FIG. 16B is a diagram illustrating a state in which the magneto-encephalogram distribution map 141 is displayed as the downsized image 141a is touched or clicked, according to the present modification of the second embodiment.

According to the present modification as illustrated in FIG. 16B, in addition to the effect as achieved in FIG. 16A, the magneto-encephalogram distribution maps that correspond to the downsized images that are not touched or clicked are hidden from view. In this respect, the visual recognizability of waveform further improves according to the present modification as illustrated in FIG. 16B.

Note that the configuration of the present modification may be applied to the measurement and recording screen as illustrated in FIG. 14. Moreover, the magneto-encephalogram distribution maps 141 and 142 and the brain-wave distribution map 130 as illustrated in FIG. 16A or FIG. 16B may be configured in a movable manner.

Seventh Modification of Second Embodiment

Figure 17:
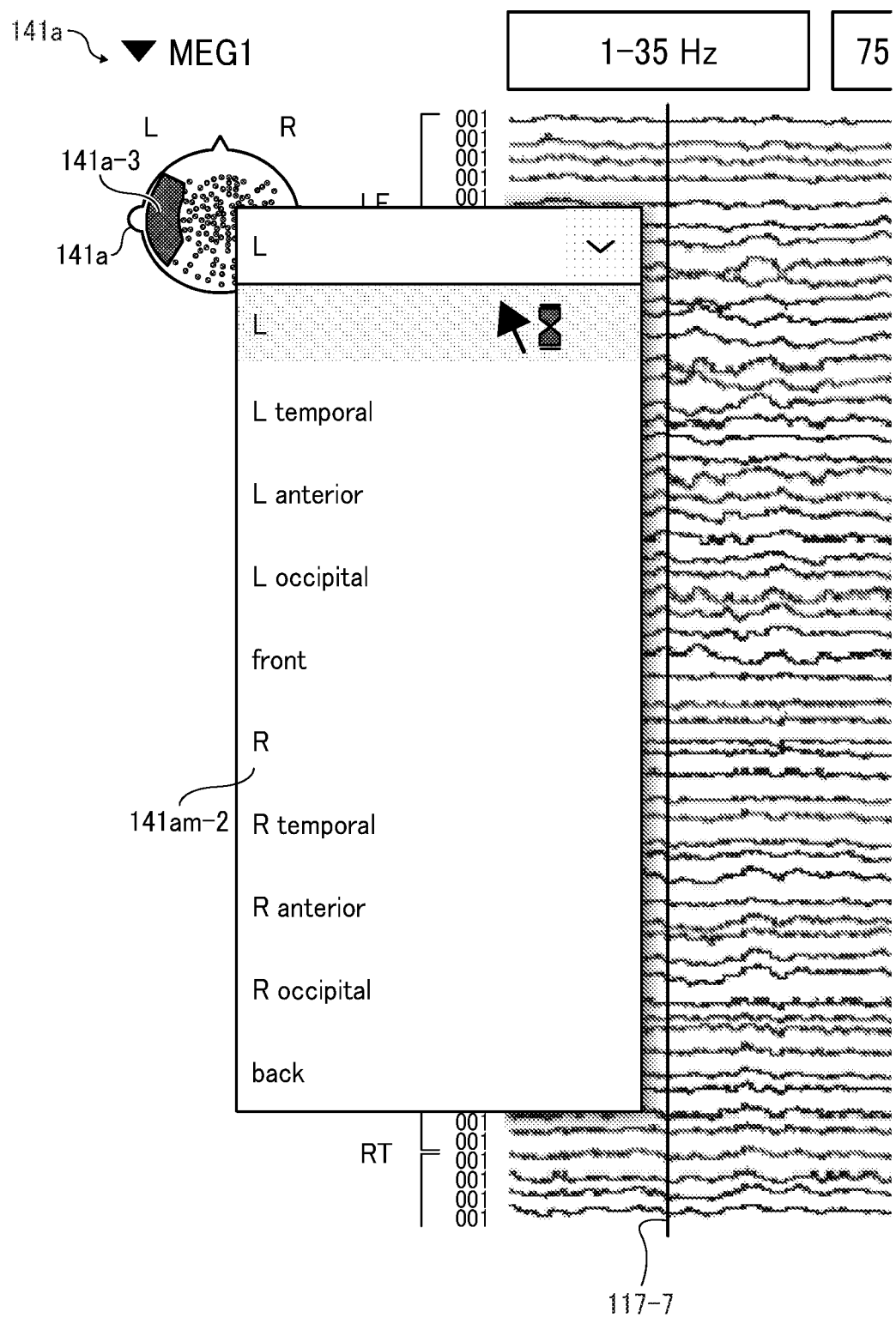
FIG. 17 is a diagram illustrating a method of selecting a target region on a downsized image, according to an embodiment of the present disclosure.

Next, a seventh modification of the second embodiment of the present disclosure is described. When the number of sensors (sensor imagery) 141a-3 displayed in the downsized image 141a is to be changed, the analyst right-clicks the downsized image 141a using an operation unit such as a mouse and, as illustrated in FIG. 17, the display controller 251 controls the display to display a pull-down menu 141am-2 that indicates a target region of the sensors. Then, the analyst selects a desired target region from this pull-down menu 141am-2. Once a target region is selected, the display controller 251 controls the display to switch the waveforms in the waveform display area 103 to the waveforms that correspond to the selected sensors. Moreover, the display controller 251 controls the display to switch from the range of the selected sensors 141a-3 displayed in the downsized image 141a to the display of the range corresponding to the selected sensors. The data of the preset target regions stored in the memory may be output to the pull-down menu 141am-2 and displayed thereon, or the analyst may individually define the regions as desired in the pull-down menu 141am-2. Alternatively, the target regions may be selected as desired from some patterns of target regions that are registered in advance, and the selected target regions may be displayed in the pull-down menu 141am-2.

As described above, according to the present modification of the second embodiment, the target region of the sensors is configurable while viewing the downsized image 141a from the above. Due to this configuration, the shift of the line of vision of the analyst can be reduced with reference to the downsized image 141a, and the operability or efficiency improves. Moreover, the target region of the sensors is configurable without viewing the magneto-encephalogram distribution map 141. Accordingly, the enlarged state of the waveform display areas can be maintained, and it is no longer necessary to view the magneto-encephalogram distribution map 141 when configuring the target region of the sensors. Accordingly, the operability or efficiency further improves.

According to the present modification of the second embodiment, a method of selecting sensors on the downsized image 141a is different from a method of selecting sensors on the magneto-encephalogram distribution map 141. In particular, sensors can be selected on a single-sensor-by-single-sensor basis on the magneto-encephalogram distribution map 141 in addition to the selection under the preset conditions, but the sensors on the downsized image 141a are selectable only under the preset conditions. As described above, only when the sensors are target specifically, the target region of the sensors are configured while viewing the normal-sized screen. Accordingly, the operability or efficiency further improves.

Alternatively, each one of the preset regions may be indicated with a different color. Due to such a configuration, the visual recognizability further improves.

By way of example, the present modification has been described with reference to the downsized image 141a. However, the present modification may be applied to the other downsized images 142a and 130a. Moreover, the configuration of the present modification may be applied to the measurement and recording screen as illustrated in FIG. 14.

Figure 20:
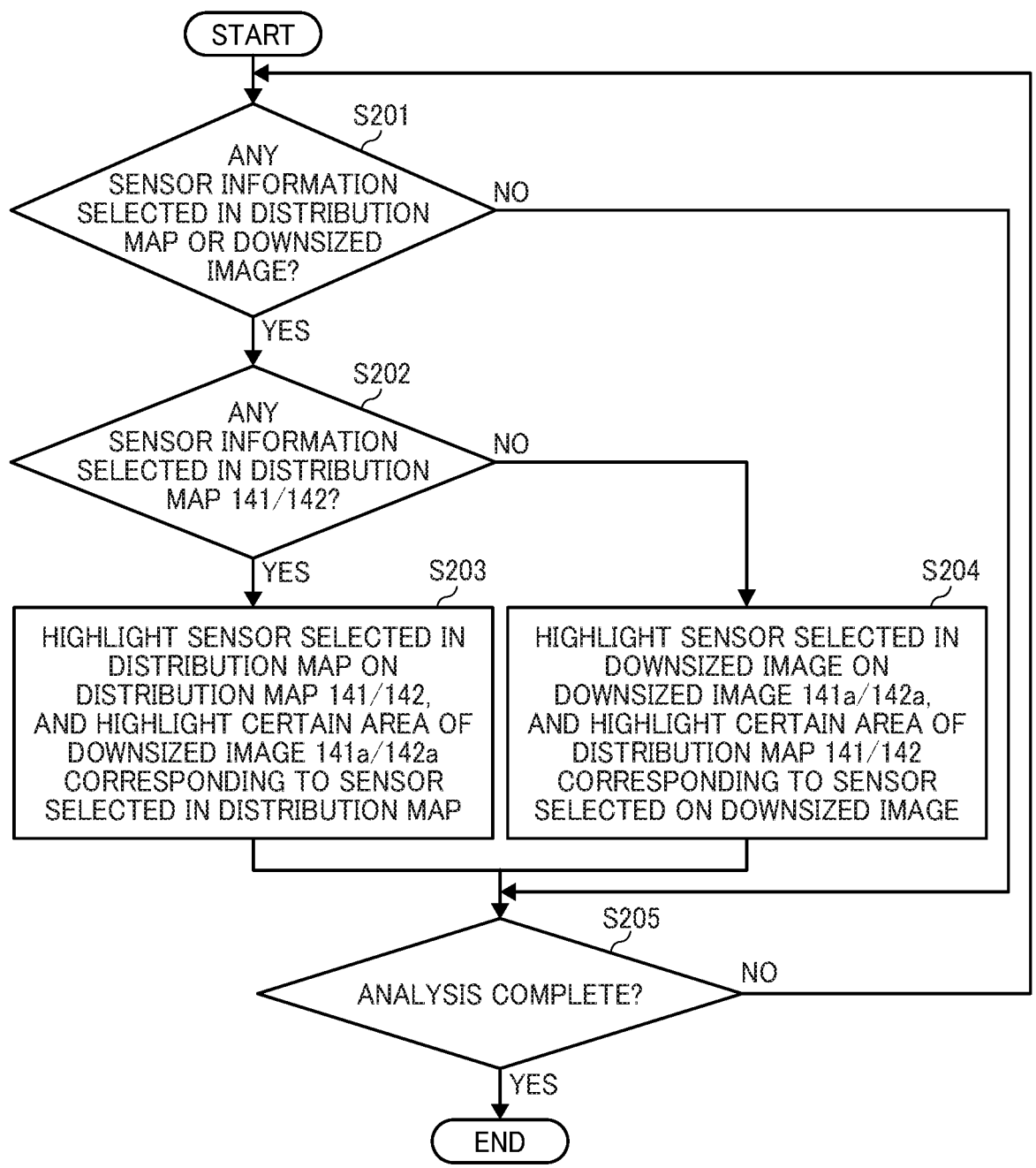
FIG. 20 is a second flowchart of displaying operation performed on a magneto-encephalogram distribution map and a downsized image, according to an embodiment of the present disclosure.

FIG. 20 is a second flowchart of a displaying operation performed on the magneto-encephalogram distribution map 141 and the downsized image 141a, according to the present embodiment.

The determining unit 55 determines whether the selection of desired sensor imagery in the magneto-encephalogram distribution map 141 and the downsized image 141a as illustrated in FIG. 13 or FIG. 16 is accepted by the acceptance unit 52 (step S201). The selection of sensor imagery is performed by the person who records the data or the analyst. Then, when the determining unit 55 determines that the selection is accepted (YES in the step S201), the determining unit 55 further determines whether the selection of desired sensor imagery in the magneto-encephalogram distribution map 141 as illustrated in FIG. 13 or FIG. 16 is accepted (step S202).

Subsequently, when the determining unit 55 determines that the selection of desired sensor imagery in the magneto-encephalogram distribution map 141 is accepted (YES in the step S202), the display controller 251 controls the display to display the selected dots of the sensor imagery in a color distinguishable from the unselected dots of the sensor imagery, and controls the display to fill the same region of the downsized image 141a corresponding to the region selected in the magneto-encephalogram distribution map 141 (step S203).

On the other hand, when it is determined by the determining unit 55 that the target region of the magnetic sensors that are preset on the downsized image 141a by a person who records the data or an analyst have been selected (NO in the step S202) the display controller 251 highlights that region in the downsized image, and also in the magneto-encephalogram distribution map 141, highlights the selected dots of the sensor imagery as above in a color distinguishable from the unselected dots of the sensor imagery (step S203). When it is determined by the determining unit 55 that no sensor image has been selected in the step S201, the process proceeds to a step S205.

Subsequently, when a region of magnetic sensors is further selected (YES in the step S205), the processes in the steps S201 to S204 are repeated. On the other hand, when the processes in the steps S201 to S204 are not performed and the analyzing processes are to be terminated (YES in the step S205), the present process is terminated. Note that the processes are performed for the magneto-encephalogram distribution map 142 and the downsized image 142a in a similar manner to the above.

Third Embodiment

In the second embodiment of the present disclosure, the downsized images 141a and 142a are arranged on the left of the channel axis 104, and the regions of the downsized images 141a and 142a corresponding to the regions of the magnetic sensors selected on the magneto-encephalogram distribution maps 141 and 142 are filled with a brighter or darker color. By contrast, the present embodiment is different from the second embodiment of the present disclosure in that the downsized images are arranged above time axis 122 and the multiple checkboxes of a group of downsized images similar to the regions of the magnetic sensors selected on the magneto-encephalogram distribution maps 141 and 142 are checked.

Figure 22:
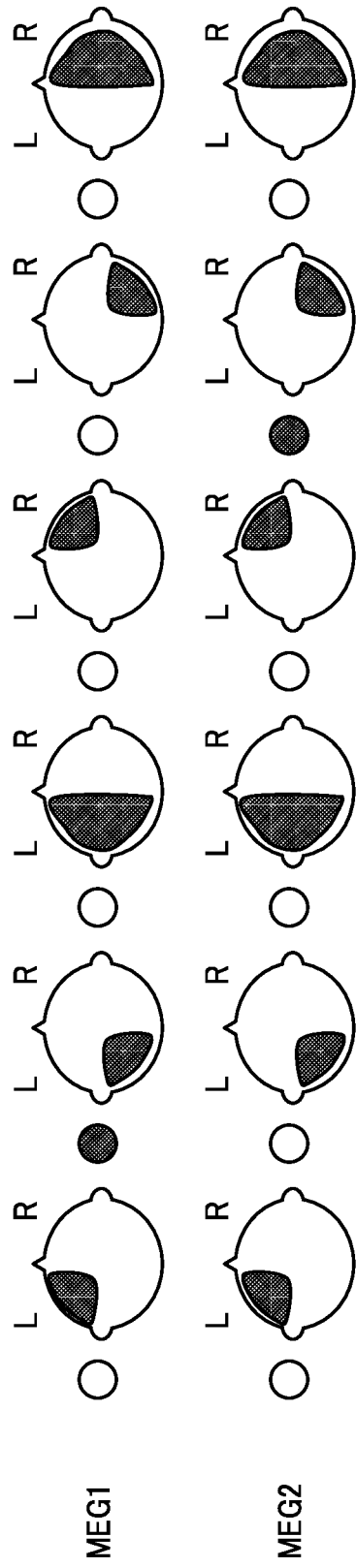
FIG. 22 is a diagram illustrating a set of downsized images according to a first modification of an embodiment of the present disclosure.

FIG. 22 is a diagram illustrating a third embodiments of the present disclosure.

In FIG. 22, the ranges of magnetic sensors displayed in the waveform display area 101 are denoted by MEG 1, and the ranges of magnetic sensors displayed in the waveform display area 102 are denoted by MEG 2. Next to the titles MEG 1 and MEG 2, a plurality of pairs of a checkbox and the figure of the external shape of a head are displayed. It is desired that the options illustrated in FIG. 22 correspond to the options given in FIG. 7C. Each of the ranges that is filled with a brighter or darker color in the external shape of the head indicates the range of target magnetic sensors. These options target as illustrated in FIG. 22 may be registered in the data storage unit 254 in advance, or may be registered or modified as desired by a technician or an analyst.

When a person who records the data or an analyst selects desired magnetic sensors in the magneto-encephalogram distribution maps 141 and 142 from the pull-down menu 141m-2 (see FIG. 7C), the selected dots of the sensor imagery are displayed on the magneto-encephalogram distribution maps 141 and 142 in a color distinguishable from the unselected dots of the sensor imagery, and the checkboxes of the group of downsized images MEG1 and MEG2 whose selected regions are the same as the regions selected on the magneto-encephalogram distribution maps 141 and 142 are checked.

On the other hand, when the range of desired magnetic sensors on the magneto-encephalogram distribution map is selected by a person who records the data or an analyst as in FIG. 7A, the selected dots of the sensor imagery are displayed on the magneto-encephalogram distribution map in a color distinguishable from the unselected dots of the sensor imagery, and the checkboxes of a group of downsized images most similar to the regions selected on the magneto-encephalogram distribution map are checked.

When any one of the checkboxes of the downsized images is ticked or checked by a person who records the data or an analyst, the selected dots of the sensor imagery are displayed in a color distinguishable from the unselected dots of the sensor imagery also on the magneto-encephalogram distribution map.

Due to the configuration as described above, the work of executing a program can be reduced, and the operability further improves. As the groups of downsized images MEG1 and MEG2 are displayed in the waveform display area 101 in the present embodiment, the duration of time of the waveform to be displayed, for example, in the waveform display area 101 can be broadened.

Moreover, in the present embodiment, the order in which the waveform display areas are arranged (i.e., the order in which 101 and 102 are displayed in a top-to-bottom direction) is matched to the order in which the downsized images of magnetic sensors are arranged (i.e., the order in which MEG1 and MEG2 are arranged in a top-to-bottom direction). Accordingly, the viewability of the target region of magnetic sensors and the viewability of the waveforms in the waveform display area improve. Further, when a mouse is moved to a checkbox ticked or checked in the group of downsized images MEG1 or a figure of the external shape of a head, the corresponding waveform display area may be highlighted. Accordingly, the viewability of the target region of magnetic sensors and the viewability of the waveforms in the waveform display area improve.

Figure 23:
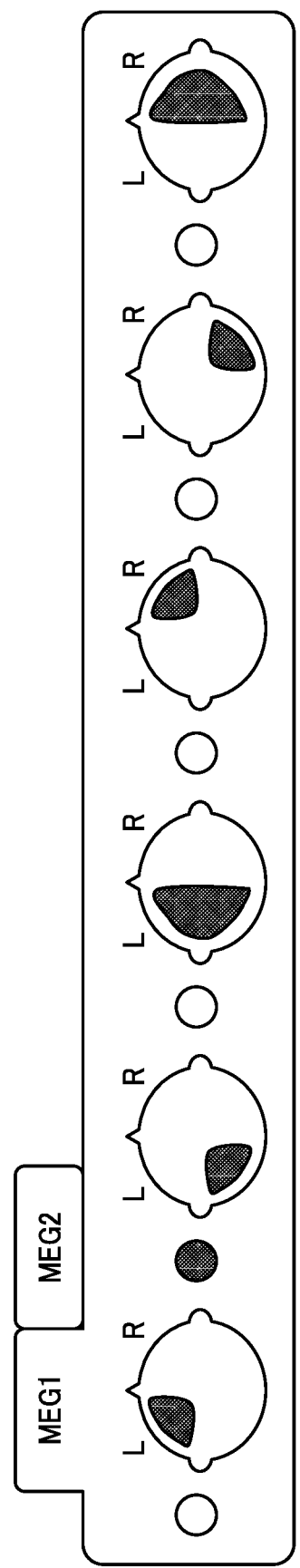
FIG. 23 is a diagram illustrating a set of downsized images according to a second modification of an embodiment of the present disclosure.

A method of displaying downsized images may be in a state as illustrated in FIG. 23. FIG. 23 is different from FIG. 22 in the configuration that the group of downsized images MEG1 and the group of downsized images MEG2 are tabbed and displayed. According to the present embodiment, the space occupied by the display area of downsized images in the up-and-down directions can be reduced compared with FIG. 22. Accordingly, the area of the waveform display areas in the up-and-down directions can be increased, and the visual recognizability of waveform improves.

Fourth Embodiment

In the second embodiment, both the downsized images and the magneto-encephalogram distribution maps are displayed, or the magneto-encephalogram distribution maps are switched between a displayed state and a hidden state. By contrast, in the present embodiment, only the downsized images are displayed. When it is desired that the target region of magnetic sensors be configured more closely and carefully in a similar manner to the magneto-encephalogram distribution maps, the target region of magnetic sensors are more closely and carefully selected from a menu, and configured on a separate screen. Once the target region of magnetic sensors is configured on the separate screen and the screen is closed (or once the registration key is touched or clicked) in the present embodiment, the region configured on the downsized image is reflected as illustrated in FIG. 14 or FIG. 15. Due to the configuration as described above, the layout of the screen is simplified, and thus the visual recognizability and operability improve.

Figure 24:
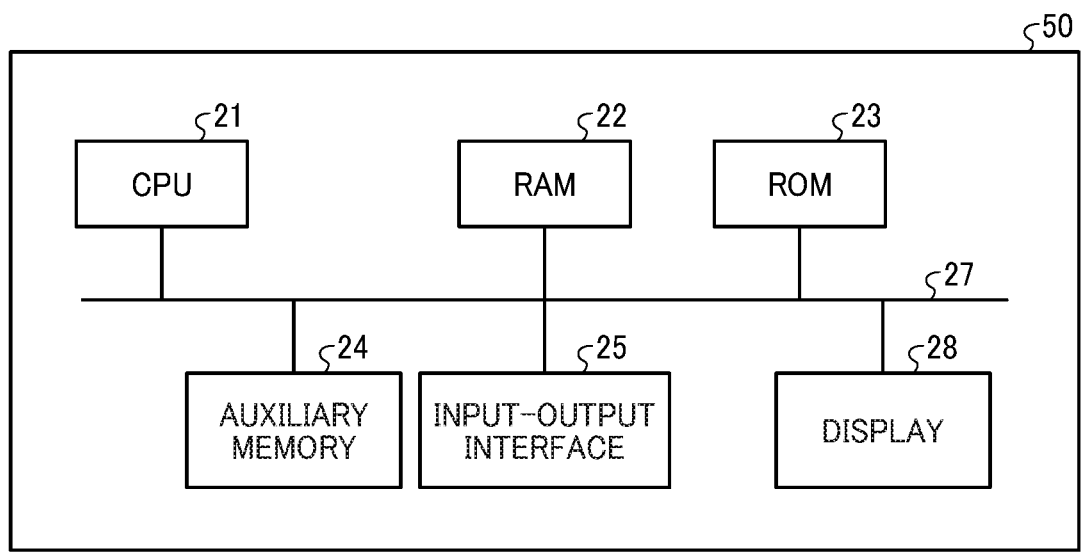
FIG. 24 is a block diagram illustrating a hardware configuration of an information processing device according to an embodiment of the present disclosure.

FIG. 24 is a schematic block diagram illustrating a hardware configuration of the information processing device 50, according to the present embodiment.

The information processing device 50 is provided with a central processing unit (CPU, processor) 21, a random access memory (RAM) 22, a read only memory (ROM) 23, an auxiliary storage device 24, an input-output interface 25, and a display 28, and these elements are interconnected through a bus 27.

The CPU 21 controls the entire operation of the information processing device 50, and performs various kinds of information processing. Moreover, the CPU 21 executes an information displaying program stored in the ROM 23 or the auxiliary storage device 24, to adjust the display of the measurement and recording screen and the analyzing screen. The RAM 22 is used as a work area of the CPU 21, and may include a nonvolatile RAM in which a desired control parameter or desired data are stored. For example, the ROM 23 stores a basic input and output program. The ROM 23 may also store the information displaying program according to the present embodiment. The auxiliary storage device 24 is a storage device such as a solid state disk (SSD) and a hard disk drive (HDD), and stores, for example, a control program to control the operation of the information processing device 50, various kinds of data used to operate the information processing device 50, and files. The input-output interface 25 is provided with both a user interface such as a touch panel, a keyboard, a display screen, and an operation key and a communication interface that takes in data from various kinds of sensors or the server 40 and outputs the analyzed data to another external electronic device. The display 28 is a device for displaying various kinds of information thereon. The measurement and recording screen and the analyzing screen are displayed on the display 28, and the screen of the display 28 is updated in response to input and output operation through the input-output interface 25.

Figure 25:
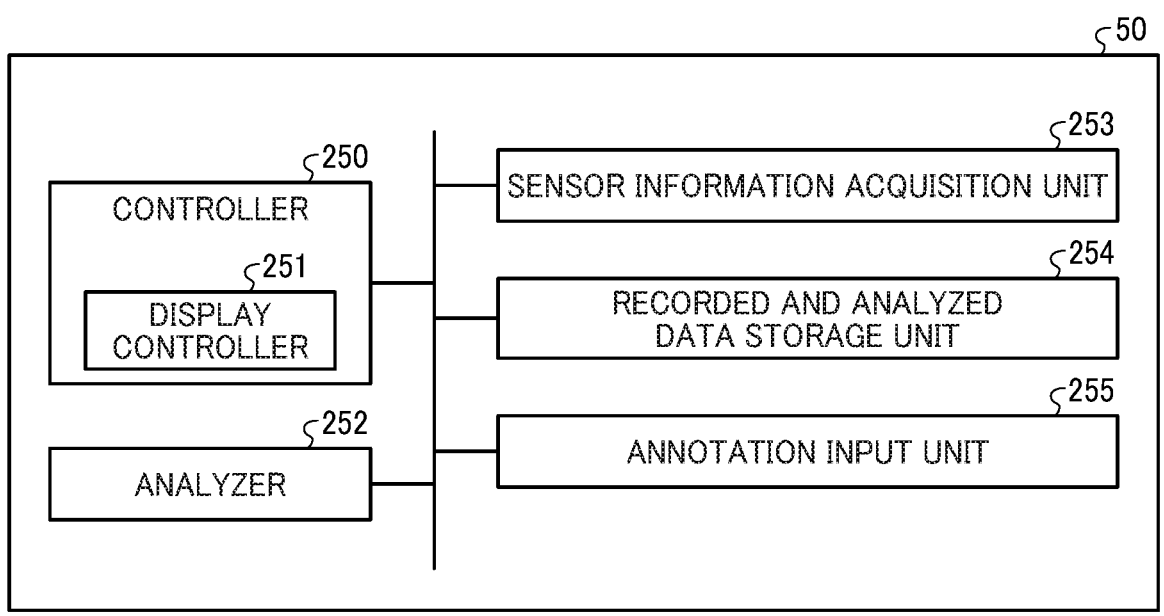
FIG. 25 is a functional block diagram of an information processing device according to an embodiment of the present disclosure.

FIG. 25 is a functional block diagram of the information processing device 50 according to the present embodiment.

The information processing device 50 includes a controller 250, an analyzer 252, a sensor information acquisition unit 253, a data storage unit 254, and an annotation input unit 255. The controller 250 includes a display controller 251 that controls the visual display of the information processing device 50.

The sensor information acquisition unit 253 obtains sensor information from the measurement device 3 or the server 40. The annotation input unit 255 inputs annotation data to be added to the sensor information. The analyzer 252 analyzes the collected sensor information. The analysis of sensor information includes signal waveform analysis, analysis of singular point of amplitude, and analysis of magnetic field of the brain including the direction of a current dipole. In other words, in the present embodiment, the analyzer 252 serves as an estimation unit and functions to estimate a signal source that corresponds to the annotation selected on the analyzing screen. The display controller 251 controls the visual display when the sensor information is measured and recorded or analyzed, according to the above-described method. The data storage unit 254 stores the measurement data and the analytical results. When an annotation is added to the signal waveform during the measurement and recording, the added annotation is also stored in association with the time at which the signal waveform is obtained. The functions of the controller 250 including the display controller 251 may be implemented as the CPU 21 illustrated in FIG. 24 develops a program stored in a memory such as the ROM 23 onto the RAM 22 and executes the developed program. The functions of the analyzer 252 may also be implemented as the CPU 21 develops a program stored in a memory such as the ROM 23 onto the RAM 22 and executes the developed program. However, no limitation is intended thereby. For example, at least some of these functions of the controller 250 and the analyzer 252 may be implemented by a dedicated hardware circuit such as a semiconductor integrated circuit. The functions of the sensor information acquisition unit 253 and the annotation input unit 255 are implemented by the input-output interface 25. The functions of the data storage unit 254 are implemented by the ROM 23 or the auxiliary storage device 24.

Numerous additional modifications and variations are possible in light of the above teachings. It is therefore to be understood that within the scope of the appended claims, the embodiments of the present disclosure may be practiced otherwise than as specifically described herein. For example, elements and/or features of different illustrative embodiments may be combined with each other and/or substituted for each other within the scope of this disclosure and appended claims. For example, some of the elements described in the above embodiments may be removed. Further, elements according to varying embodiments or modifications may be combined as appropriate.

A program for the biomedical-signal measuring system 1 according to the above-described embodiment and variation may be installed for distribution in any desired computer-readable recording medium such as a compact disc, a read-only memory (CD-ROM), a flexible disk (FD), a compact disc-recordable (CD-R), and a digital versatile disk (DVD), a universal serial bus (USB) in a file format installable or executable by a computer, or may be provided or distributed via network such as Internet. Alternatively, various kinds of programs may be integrated in advance, for example, into a ROM inside the device for distribution.

By way of example, a downsized image of a magneto-encephalogram distribution map is described in the present disclosure. However, no limitation is intended thereby, and the embodiments of the present disclosure may be applied to different kinds of setting area. For example, as illustrated in FIG. 26A and FIG. 26B, the embodiments of the present disclosure may be applied to a magneto-cardiograph.

Figure 26A:
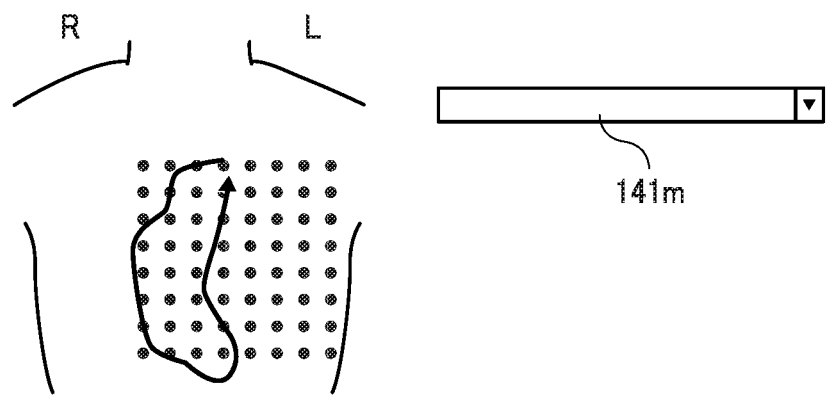
FIG. 26A and FIG. 26B are diagrams each illustrating a distribution map of a magneto-cardiograph, according to an embodiment of the present disclosure.
Figure 26B:
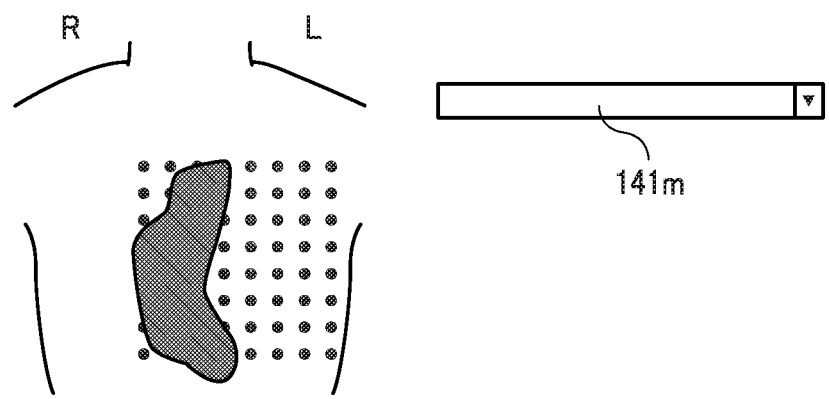

FIG. 26A and FIG. 26B are diagrams each illustrating a distribution map of a magneto-cardiograph, according to the present embodiment.

FIG. 26A and FIG. 26B correspond to FIG. 7A and FIG. 7B, respectively.

Figure 27A:
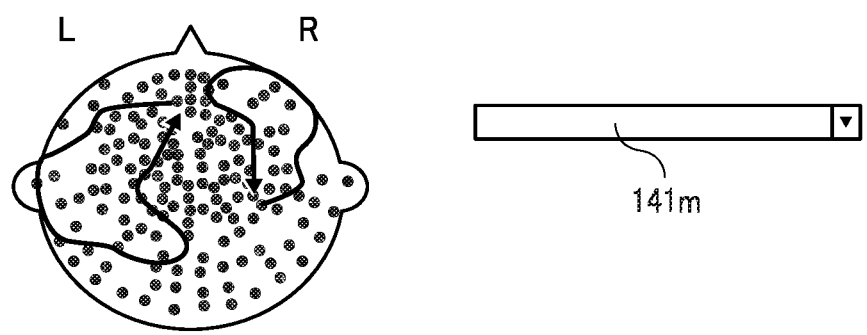
FIG. 27A and FIG. 27B are diagrams each illustrating a magneto-encephalogram distribution map from which a plurality of regions of magnetic sensors can be selected, according to an embodiment of the present disclosure.
Figure 27B:
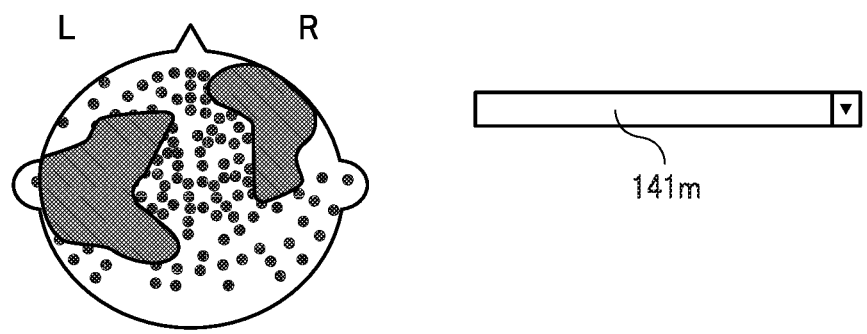

As illustrated in FIG. 27A and FIG. 27B, it may be configured such that a plurality of regions of magnetic sensors are selectable.

FIG. 27A and FIG. 27B are diagrams each illustrating a magneto-encephalogram distribution map from which a plurality of regions of magnetic sensors can be selected, according to an embodiment of the present disclosure.

FIG. 27A and FIG. 27B correspond to FIG. 7A and FIG. 7B, respectively. In the present embodiment, the regions may be filled with the same color, or may separately be filled with different colors. Moreover, such a configuration may be applied not only to magneto-encephalogram distribution maps but also to downsized images.

Figure 28A:
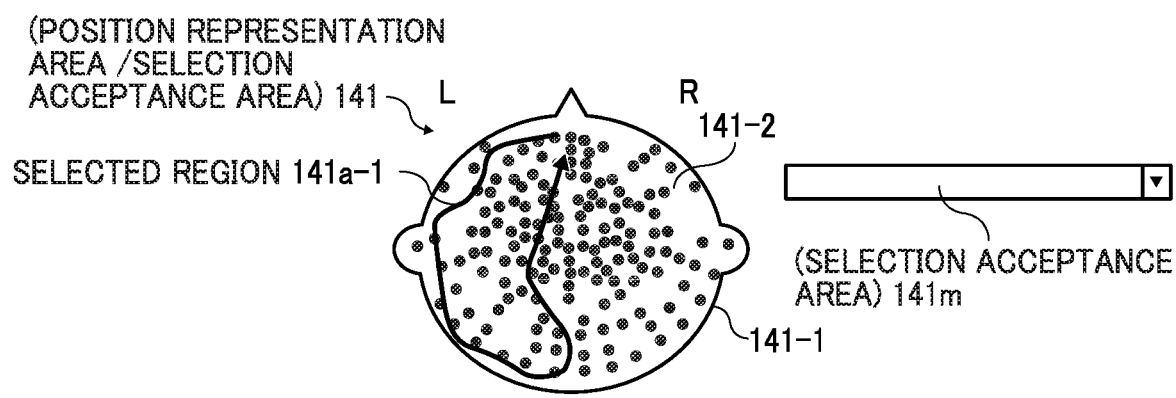
FIG. 28A and FIG. 28B are diagrams each illustrating a modification of a distribution map according to an embodiment of the present disclosure.
Figure 28B:
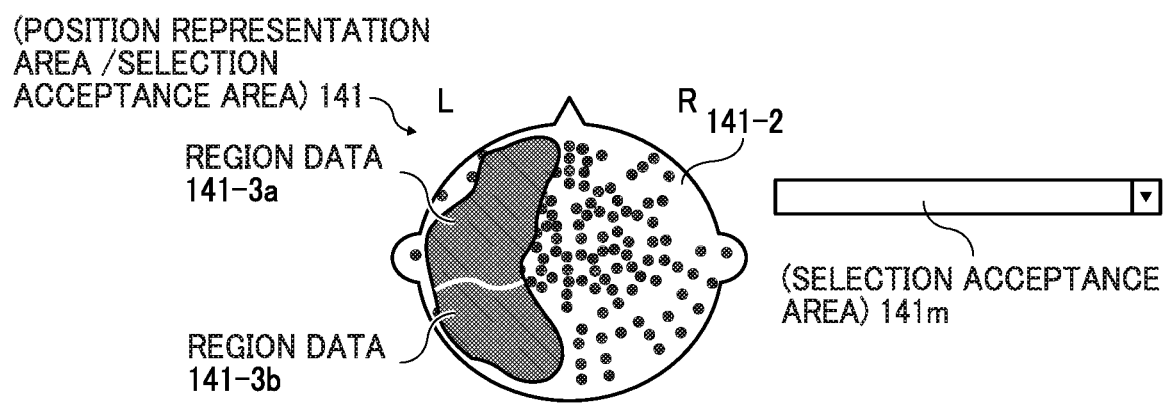

When a region of magnetic sensors is selected, the segments of the selected region may separately displayed with a different color depending on the site of the head. For example, as illustrated in FIG. 28A, once a target region 141a-1 including a plurality of pieces of sensor imagery is specified, as illustrated in FIG. 28B, each of region data 141-3a and region data 141-3b is separately displayed with a different color within the selected region. The information about the sites of the head and the colors to be displayed depending on each site of the head are stored in the memory in advance, and the region data 141-3a and the region data 141-3b are displayed based on the information stored in the memory. In a similar manner to the above, this configuration may be applied not only to magneto-encephalogram distribution maps but also to downsized images.

The term "test subject" as used in the above description is used merely by way of example, and includes not only humans but also, for example, dogs or cats, or laboratory rats. Each one of the magneto-encephalogram distribution maps 141 and 142 is an example of a large selection acceptance area, and each one the downsized images 141a and 142a is an example of a small selection acceptance area.

Numerous additional modifications and variations are possible in light of the above teachings. It is therefore to be understood that within the scope of the appended claims, the disclosure of the present disclosure may be practiced otherwise than as specifically described herein. For example, elements and/or features of different illustrative embodiments may be combined with each other and/or substituted for each other within the scope of this disclosure and appended claims.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An information processing device, comprising:
    circuitry to
        display, on a display, a position representation area, including an image including a first graphic symbol of a body part, and, for each sensor of a group of sensors that can detect biomedical signals of a test subject, a second graphic symbol indicating a position of the sensor, each second graphic symbol being superimposed on the first graphic symbol of the body part;
        display, on the display, a selection acceptance area accepting selection of a plurality of positions of a plurality of desired sensors, the plurality of positions being selected from the group of sensors by user input; and
        display, on the display, a waveform display area displaying a waveform output from the plurality of desired sensors corresponding to the plurality of selected positions,
    wherein the circuitry is further configured to, in response to the selection of the plurality of positions of the plurality of desired sensors, (1) display, in the position representation area, the image including the first graphic symbol of the body part, and the second graphic symbols of each sensor in the group of sensors, and (2) separately display a reduced-size version of the image including the first graphic symbol of the body part, the second graphic symbols of each sensor in the group of sensors, and a closed contour of a region within the first graphic symbol encompassing only the second graphic symbols of the plurality of selected positions, the reduced-size version being smaller in size than the displayed image, wherein the closed contour is displayed within the reduced-size version of the image, but not within the image displayed in the position representation area.

2. The information processing device according to claim 1, wherein the circuitry is further configured to display the position representation area, which includes the selection acceptance area, and in response to the selection of the plurality of positions of the plurality of desired sensors, cease displaying, the graphic symbols of those sensors, of the group of sensors, that were not selected by the user input.

3. The information processing device according to claim 1, wherein the circuitry is further configured to display the position representation area and the waveform display area parallel to each other in a direction of propagation of the waveform.

4. The information processing device according to claim 3, wherein the circuitry is further configured to display the position representation area and the waveform display area next to each other.

5. The information processing device according to claim 1, wherein the circuitry is further configured to display the image in a first position representation region, and display the reduced-size version of the image in a second position representation region, the first position representation region having a size larger than a size of the second position representation region.

6. The information processing device according to claim 5, wherein the circuitry is further configured to display the selection acceptance area, which includes:
    a first selection acceptance area that accepts selection of the plurality of positions by accepting designation of a range including the plurality of positions of the plurality of desired sensors from the group of sensors displayed in the first position representation area; and
    a second selection acceptance area that accepts selection of the plurality of positions by displaying a list through which the plurality of positions of the plurality of desired sensors are collectively selectable from the group of sensors displayed in the second position representation area, the first selection acceptance area having a size larger than a size of the second selection acceptance area.

7. The information processing device according to claim 6,
    wherein the circuitry is further configured to display the first selection acceptance area, which accepts designation of a range including the plurality of positions, and
    the first position representation area displays a specific option of region data that indicates a region closest to a region designated from among a plurality of options of region data determined in advance.

8. A biomedical-signal measuring system, comprising:
    the information processing device according to claim 1; and
    a measurement device provided with the group of sensors that detect biomedical signals of the test subject.

9. An information processing device, comprising:
    circuitry to
        display, on a display, a position representation area, including an image including a first graphic symbol of a body part, and, for each sensor of a group of sensors that can detect biomedical signals of a test subject, a second graphic symbol indicating a position of the sensor, each second graphic symbol being superimposed on the first graphic symbol of the body part;
        display, on the display, a selection acceptance area accepting a plurality of positions of a plurality of desired sensors, the plurality of positions being selected from the group of sensors by user input; and
        display, on the display, a waveform display area displaying a waveform output from the plurality of desired sensors corresponding to the plurality of selected positions,
    wherein the circuitry is further configured to, in response to the selection of the plurality of positions of the plurality of desired sensors, (1) graphically enlarge the displayed second graphical symbols of the plurality of selected positions in comparison to positions of sensors, of the group of sensors, that were not selected by the user input, and display the graphically enlarged second graphic symbols in the position representation area, and (2) display a reduced-size version of the image including the second graphic symbols of each sensor in the group of sensors, the reduced-size version of the image being smaller in size than the image displayed in the position representation area.

10. The information processing device according to claim 9, wherein the circuitry is further configured to display the position representation area, which includes the selection acceptance area.

11. The information processing device according to claim 9, wherein the circuitry is further configured to display the position representation area and the waveform display area parallel to each other in a direction of propagation of the waveform.

12. The information processing device according to claim 11, wherein the circuitry is further configured to display the position representation area and the waveform display area next to each other.

13. The information processing device according to claim 9, wherein the circuitry is further configured to display the position representation area, which includes:
- a first position representation area indicating a position of each of the group of sensors; and
- a second position representation area indicating a position of each of the group of sensors, the first position representation area having a size larger than a size of the second position representation area.

14. The information processing device according to claim 13, wherein the circuitry is further configured to display the selection acceptance area, which includes:
- a first selection acceptance area that accepts selection of the plurality of positions by accepting designation of a range including the plurality of positions of the plurality of desired sensors from the group of sensors displayed in the first position representation area; and
- a second selection acceptance area that accepts selection of the plurality of positions by displaying a menu through which the plurality of positions of the plurality of desired sensors are collectively selectable from the group of sensors displayed in the second position representation area, the first selection acceptance area having a size larger than a size of the second selection acceptance area.

15. The information processing device according to claim 14,
wherein the circuitry is further configured to display the first selection acceptance area, which accepts designation of a range including the plurality of positions, and
the first position representation area displays a specific option of region data that indicates a region closest to a region designated from among a plurality of options of region data determined in advance.

16. A biomedical-signal measuring system, comprising:
the information processing device according to claim 9; and
a measurement device provided with the group of sensors that detect biomedical signals of the test subject.

17. A method of displaying biomedical signals of a test subject, the method comprising:
- displaying a position representation area, including an image including a first graphic symbol of a body part, and, for each sensor of a group of sensors that can detect the biomedical signals of the test subject, a second graphic symbol indicating a position of the sensor, each second graphic symbol being superimposed on the first graphic symbol of the body part;
- displaying a selection acceptance area accepting a plurality of positions of a plurality of desired sensors, the plurality of positions being selected from the group of sensors by user input; and
- displaying a waveform display area displaying a waveform output from the plurality of desired sensors corresponding to the plurality of selected positions,
- wherein the step of displaying the position representation area includes, in response to the selection of the plurality of positions of the plurality of desired sensors, (1) displaying, in the position representation area, the image including the first graphic symbol of the body part, and the second graphic symbols of each sensor in the group of sensors, and (2) separately displaying a reduced-size version of the image including the first graphic symbol of the body part, the second graphic symbols of each sensor in the group of sensors, and a closed contour of a region within the first graphic symbol encompassing only the second graphic symbols of the plurality of selected positions, the reduced-size version being smaller in size than the displayed image, wherein the closed contour is displayed within the reduced-size version of the image, but not within the image displayed in the position representation area.

18. A computer-readable non-transitory recording medium storing a program for causing a computer to execute a method of displaying biomedical signals of a test subject, the method comprising:
- displaying a position representation area, including an image including a first graphic symbol of a body part, and, for each sensor of a group of sensors that can detect the biomedical signals of the test subject, a second graphic symbol indicating a position of the sensor, each second graphic symbol being superimposed on the first graphic symbol of the body part;
- displaying a selection acceptance area accepting a plurality of positions of a plurality of desired sensors, the plurality of positions being selected from the group of sensors by user input; and
- displaying a waveform display area displaying a waveform output from the plurality of desired sensors corresponding to the plurality of selected positions,
- wherein the step of displaying the position representation area includes, in response to the selection of the plurality of positions of the plurality of desired sensors, (1) displaying, in the position representation area, the image including the first graphic symbol of the body part, and the second graphical symbols of each sensor in the group of sensors, and (2) separately displaying a reduced-size version of the image including the first graphic symbol of the body part, the second graphic symbols of each sensor in the group of sensors, and a closed contour of a region within the first graphic symbol encompassing only the second graphic symbols of the plurality of selected positions, the reduced-size version being smaller in size than the displayed image, wherein the closed contour is displayed within the reduced-size version of the image, but not within the image displayed in the position representation area.

19. A method of displaying biomedical signals of a test subject, the method comprising:
- displaying a position representation area, including an image including a first graphic symbol of a body part, and, for each sensor of a group of sensors that can detect the biomedical signals of the test subject, a second graphic symbol indicating a position of the sensor, each second graphic symbol being superimposed on the first graphic symbol of the body part;
- displaying a selection acceptance area accepting a plurality of positions of a plurality of desired sensors, the plurality of positions being selected from the group of sensors by user input;
- displaying a waveform display area displaying a waveform output from the plurality of desired sensors corresponding to the plurality of selected positions; and
- in response to the selection of the plurality of positions of the plurality of desired sensors, (1) graphically enlarging the displayed second graphical symbols of the plurality of selected positions in comparison to positions of sensors, of the group of sensors, that were not selected by the user input, and displaying the graphically enlarged second graphical symbols in the position representation area, and (2) separately displaying a reduced-size version of the image including the second graphic symbols of each sensor in the group of sensors, the reduced-size version of the image being smaller in size than the image displayed in the position representation area.

20. A computer-readable non-transitory recording medium storing a program for causing a computer to execute a method of displaying biomedical signals of a test subject, the method comprising:

displaying a position representation area, including an image including a first graphic symbol of a body part, and, for each sensor of a group of sensors that can detect the biomedical signals of the test subject, a second graphic symbol indicating a position of the sensor, each second graphic symbol being superimposed on the first graphic symbol of the body part;

displaying a selection acceptance area accepting a plurality of positions of a plurality of desired sensors, the plurality of positions being selected from the group of sensors by user input;

displaying a waveform display area displaying a waveform output from the plurality of desired sensors corresponding to the plurality of selected positions; and in response to the selection of the plurality of positions of the plurality of desired sensors, (1) graphically enlarging the displayed second graphical symbols of the plurality of selected positions in comparison to positions of sensors, of the group of sensors, that were not selected by the user input, and displaying the graphically enlarged second graphical symbols in the position representation area, and (2) separately displaying a reduced-size version of the image including the second graphic symbols of each sensor in the group of sensors, the reduced-size version of the image being smaller in size than the image displayed in the position representation area.

* * * * *